(12) United States Patent
Mosrin et al.

(10) Patent No.: US 11,072,609 B2
(45) Date of Patent: Jul. 27, 2021

(54) METHOD FOR PREPARING HALOGENATED IMIDAZOPYRIDINE DERIVATIVES

(71) Applicants: Bayer Aktiengesellschaft, Leverkusen (DE); Bayer CropScience Aktiengesellschaft, Monheim am Rhein (DE)

(72) Inventors: Marc Mosrin, Cologne (DE); Ruediger Fischer, Pulheim (DE); Dominik Hager, Monheim (DE); Laura Hoffmeister, Duesseldorf (DE); Nina Kausch-Busies, Bergisch Gladbach (DE); David Wilcke, Duesseldorf (DE); Matthieu Willot, Duesseldorf (DE); Kerstin Ilg, Cologne (DE)

(73) Assignees: Bayer Aktiengesellschaft, Leverkusen (DE); Bayer CropScience Aktiengesellschaft, Monheim am Rhein (DE)

( * ) Notice: Subject to any disclaimer, the term of this patent is extended or adjusted under 35 U.S.C. 154(b) by 126 days.

(21) Appl. No.: 16/481,124

(22) PCT Filed: Feb. 5, 2018

(86) PCT No.: PCT/EP2018/052784
§ 371 (c)(1),
(2) Date: Jul. 26, 2019

(87) PCT Pub. No.: WO2018/141955
PCT Pub. Date: Aug. 9, 2018

(65) Prior Publication Data
US 2021/0094947 A1 Apr. 1, 2021

(30) Foreign Application Priority Data
Feb. 6, 2017 (EP) ..................... 17154787

(51) Int. Cl.
*C07D 471/04* (2006.01)
(52) U.S. Cl.
CPC .................. *C07D 471/04* (2013.01)
(58) Field of Classification Search
CPC .................................................. C07D 471/04
(Continued)

(56) References Cited

U.S. PATENT DOCUMENTS

| 10,087,192 B2 | 10/2018 | Fischer et al. |
| 2017/0073342 A1 | 3/2017 | Fischer et al. |

(Continued)

FOREIGN PATENT DOCUMENTS

| WO | 2010125985 A1 | 11/2010 |
| WO | 2012074135 A1 | 6/2012 |

(Continued)

OTHER PUBLICATIONS

Middleton et al., Journal of Heterocyclic Chemistry (1980), 17(8), 1757-60.*

(Continued)

*Primary Examiner* — Niloofar Rahmani
(74) *Attorney, Agent, or Firm* — Mcbee Moore & Vanik Ip, LLC

(57) ABSTRACT

The present invention relates to a method for preparing halogenated imidazopyridine derivatives of the formula (II) proceeding from compounds of the formula (I) via intermediates of the formula (IVa) or (IVb)

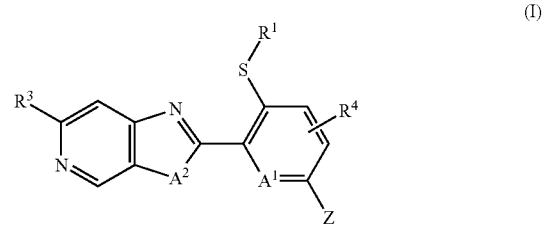

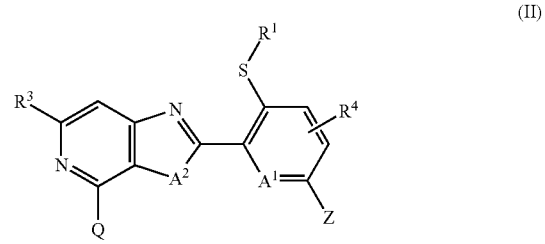

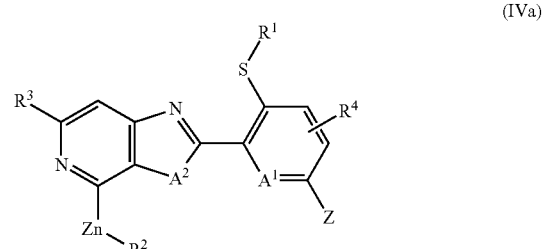

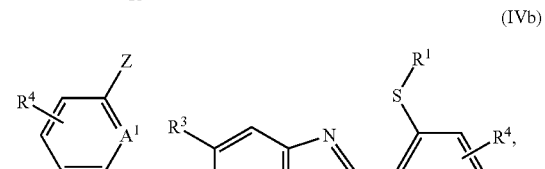

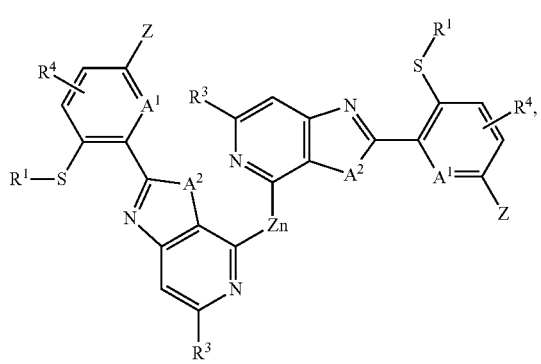

(Continued)

in which the radicals
Q, Z, $R^1$, $R^3$, $R^4$, $R^c$, $A^1$ and $A^2$ have the definitions stated. The invention further relates to such halogenated imidazopyridine derivatives, and also intermediates and the reaction products of compounds of the formula (II) to give compounds of the formula (III)

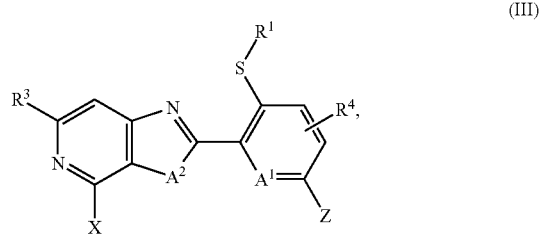

(III)

in which the specified structural elements have the definitions stated.

19 Claims, No Drawings

(58) Field of Classification Search
USPC ............................................. 546/118
See application file for complete search history.

(56) References Cited

U.S. PATENT DOCUMENTS

| 2018/0002345 A1 | 1/2018 | Fischer et al. |
| 2018/0016273 A1 | 1/2018 | Fischer et al. |
| 2018/0303097 A1 | 10/2018 | Wilcke et al. |

FOREIGN PATENT DOCUMENTS

| WO | 2012086848 A1 | 6/2012 |
| WO | 2013018928 A1 | 2/2013 |
| WO | 2013191113 A1 | 12/2013 |
| WO | 2015000715 A1 | 1/2015 |
| WO | 2015002211 A1 | 1/2015 |
| WO | 2015071180 A1 | 5/2015 |
| WO | 2015121136 A1 | 8/2015 |
| WO | 2015133603 A1 | 9/2015 |
| WO | 2015198859 A1 | 12/2015 |
| WO | 2016020286 A1 | 2/2016 |
| WO | 2016023954 A2 | 2/2016 |
| WO | 2016046071 A1 | 3/2016 |
| WO | 2016058928 A1 | 4/2016 |
| WO | 2016107831 A1 | 7/2016 |
| WO | 2016116338 A1 | 7/2016 |
| WO | 2016124557 A1 | 8/2016 |
| WO | 2016124563 A1 | 8/2016 |
| WO | 2016125621 A1 | 8/2016 |
| WO | 2016129684 A1 | 8/2016 |
| WO | 2017055185 A1 | 4/2017 |
| WO | 2017068599 A1 | 4/2017 |

OTHER PUBLICATIONS

International Search Report for PCT/EP2018/052784 dated Mar. 23, 2018.
Mosrin et al., "TMPZnCL.LiCI: A New Active Selective Base for the Directed Zincation of Sensitive Aromatics and Heteroaromatics", Organic Letters, Apr. 16, 2009, pp. 1837-1840, vol. 11, No. 8.
Mosrin et al., "Regio- and Chemoselective Multipl Functionalization of Pyrimidine Derivatives by Selective Magnesiations using TMPMgClLiCl", Organice Letters, Apr. 7, 2008, pp. 2497-2500, vol. 10, No. 12.

* cited by examiner

METHOD FOR PREPARING HALOGENATED IMIDAZOPYRIDINE DERIVATIVES

CROSS-REFERENCE TO RELATED APPLICATIONS

This application is the National Stage entry of International Application No. PCT/EP2018/052784, filed 5 Feb. 2018, which claims priority to European Patent Application No. 17154787.0, filed 6 Feb. 2017.

BACKGROUND

Field

The present invention relates to a method for preparing halogenated imidazopyridine derivatives of the formula (II)

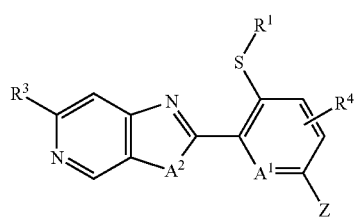

(II)

proceeding from compounds of the formula (I)

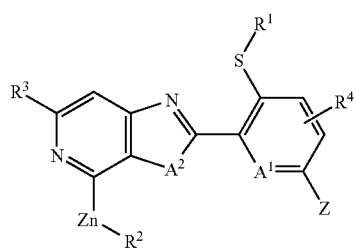

(I)

via intermediates of the formula (IVa) or (IVb)

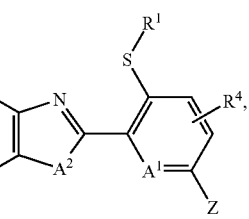

(IVa)

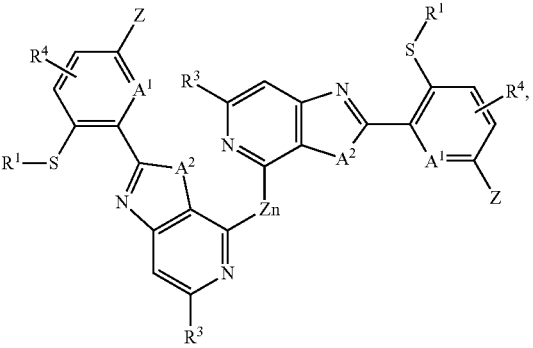

(IVb)

in which the structural elements shown in the formulae (I), (II), (IVa) and (IVb) have the definitions stated below.

The invention further relates to such halogenated imidazopyridine derivatives, and also intermediates and the reaction products of compounds of the formula (II) to give compounds of the formula (III)

(III)

in which the specified structural elements have the definitions stated below.

Description of Related Art

Halogenated imidazopyridine derivatives of the formula (II) are of great industrial significance for the pharmaceutical and agrochemical industry and are, for example, important intermediates, inter alia, in the preparation of compounds that are effective as pesticides for example.

Imidazopyridines for use as pesticides and methods for the preparation thereof are described, for example, in WO 2010/125985, WO 2012/074135, WO 2012/086848, WO 2013/018928, WO 2013/191113, WO 2015/000715, WO 2016/124563, WO 2016/124557, WO 2015/121136, WO 2015/133603, WO 2015/198859, WO 2015/002211, WO 2015/071180, WO 2016/023954, WO 2016/020286, WO 2016/046071, WO 2016/058928; WO 2016/116338, WO 2016/107831, WO 2016/129684, WO 2017/055185, WO 2017/068599 and WO 2016/125621. However, the prior art does not disclose any specific compounds of the formula (II) or (III) or methods for the preparation thereof.

In particular, the regioselective introduction of the substituents Q or X to compounds of the formula (I) represents a major challenge. This is made particularly difficult by the two chemically very similar ring systems which are coupled to each other in the compounds of the formula (I). The metallation and subsequent halogenation on the pyridine ring of such imidazopyridines has not been described to date in the literature.

Only synthetic methods for preparing uncoupled halogenated pyridine derivatives are known from the prior art. In addition, however, these chemical synthetic methods that have been described in the prior art to date very frequently make use of methods that are not economically implementable from an industrial point of view and/or have other disadvantages.

In the case of lithium bases and magnesium bases in particular, disadvantages are the low chemical yields, performing at very low temperatures and the difficult regio- and chemoselectivity of the deprotonation due to the high reactivity of these reagents. Sometimes a transmetallation with zinc salts, such as zinc chloride for example, is necessary in order to carry out further selective reactions such as Negishi cross couplings as described in Organic Letters 2008 (10), p. 2497ff. The preparation is therefore very expensive (many salts are formed) and unsuitable for industrial scale commercial processes.

With regard to the disadvantages outlined above, there is an urgent need for a simplified, industrially and economically performable method for preparing halogenated imidazopyridine derivatives, especially halogenated or substituted imidazopyridine derivatives of the formula (II) or (III). The halogenated imidazopyridine derivatives obtainable by this method sought are preferably to be obtained with good yield, high purity and in an economic manner.

SUMMARY

It has been found, surprisingly, that halogenated imidazopyridine derivatives of the formula (II) can be prepared advantageously in a method using an organozinc base, in particular even with high regio- and chemoselectivity and good yield.

The present invention accordingly provides a method for preparing compounds of the formula (II)

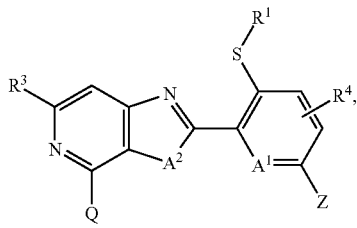

(II)

in which (configuration 1)
Q and Z are each independently halogen,
$A^1$ is nitrogen, $=N^+-O^-$ or $=C-R^5$,
$A^2$ is $-N-R^6$, oxygen or sulfur,
$R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloalkyl, $(C_3-C_6)$halocycloalkyl, $(C_3-C_6)$cyanocycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkylsulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulfinyl-$(C_1-C_6)$alkyl, $(C_1-C_6)$alkoxy-$(C_1-C_6)$alkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulfonylamino, aminosulfonyl-$(C_1-C_6)$alkyl, $(C_1-C_6)$alkylaminosulfonyl-$(C_1-C_6)$alkyl, di$(C_1-C_6)$alkylaminosulfonyl-$(C_1-C_6)$alkyl, or is $(C_1-C_6)$alkyl, $(C_1-C_6)$alkoxy, $(C_2-C_6)$alkenyl, $(C_2-C_6)$alkynyl, $(C_3-C_8)$cycloalkyl, each of which is optionally mono- or polysubstituted by identical or different substituents from the group consisting of aryl, hetaryl and heterocyclyl, where aryl, hetaryl or heterocyclyl may each optionally be mono- or polysubstituted by identical or different substituents from the group consisting of halogen, cyano, nitro, hydroxyl, amino, carboxy, carbamoyl, aminosulfonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulfinyl, $(C_1-C_6)$alkylsulfonyl, $(C_1-C_6)$alkylsulfimino, $(C_1-C_6)$alkylsulfimino-$(C_1-C_6)$alkyl, $(C_1-C_6)$alkylsulfimino-$(C_2-C_6)$alkylcarbonyl, $(C_1-C_6)$alkylsulfoximino, $(C_1-C_6)$alkylsulfoximino-$(C_1-C_6)$alkyl, $(C_1-C_6)$alkylsulfoximino-$(C_2-C_6)$alkylcarbonyl, $(C_1-C_6)$alkoxycarbonyl, $(C_1-C_6)$alkylcarbonyl, $(C_3-C_6)$trialkylsilyl and benzyl, $R^3$ is hydrogen, cyano, halogen, nitro, acetyl, hydroxyl, amino, SCN, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, cyano$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di$(C_1-C_6)$alkylaminocarbonyl, di$(C_1-C_6)$alkylaminothiocarbonyl, $(C_2-C_6)$alkenylaminocarbonyl, di$(C_2-C_6)$alkenylaminocarbonyl, $(C_3-C_8)$cycloalkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkylsulfoximino, aminothiocarbonyl, $(C_1-C_6)$alkylaminothiocarbonyl, di$(C_1-C_6)$alkylaminothiocarbonyl, $(C_3-C_8)$cycloalkylamino, —NHCO—$(C_1-C_6)$alkyl ($(C_1-C_6)$alkylcarbonylamino), or is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, tri($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl or ($C_3$-$C_8$)cycloalkylamino, $R^4$ is hydrogen, cyano, halogen, nitro, acetyl, hydroxyl, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, cyano($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di($C_1$-$C_6$)alkylaminocarbonyl, di($C_1$-$C_6$)alkylaminothiocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, NHCO—($C_1$-$C_6$)alkyl (($C_1$-$C_6$)alkylcarbonylamino), or is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, ($C_1$-$C_6$)alkylcarbonylamino, $R^5$ is hydrogen, cyano, halogen, nitro, acetyl, hydroxyl, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di($C_1$-$C_6$)alkylaminocarbonyl, di($C_1$-$C_6$)alkylaminothiocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkyl- aminothiocarbonyl, di($C_1$-$C_6$)alkylaminothiocarbonyl, ($C_3$-$C_8$)cycloalkylamino or —NHCO—($C_1$-$C_6$)alkyl (($C_1$-$C_6$)alkylcarbonylamino) and $R^6$ is ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_6$)alkyl, ($C_2$-$C_6$)haloalkynyloxy-($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkylthio-($C_1$-$C_6$)alkyl, ($C_1$-$C_6$)haloalkylthio-($C_1$-$C_6$)alkyl, ($C_1$-$C_6$)alkylsulfinyl-($C_1$-$C_6$)alkyl, ($C_1$-$C_6$)haloalkylsulfinyl-($C_1$-$C_6$)alkyl, ($C_1$-$C_6$)alkylsulfonyl-($C_1$-$C_6$)alkyl, ($C_1$-$C_6$)haloalkylsulfonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulfinyl-($C_1$-$C_6$)alkyl, ($C_1$-$C_6$)alkoxy-($C_1$-$C_6$)alkylsulfonyl-($C_1$-$C_6$)alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxycarbonyl-($C_1$-$C_6$)alkyl, ($C_1$-$C_6$)haloalkoxycarbonyl-($C_1$-$C_6$)alkyl, aminocarbonyl-($C_1$-$C_6$)alkyl, ($C_1$-$C_6$)alkylamino-($C_1$-$C_6$)alkyl, di($C_1$-$C_6$)alkylamino-($C_1$-$C_6$)alkyl or ($C_3$-$C_8$)cycloalkylamino-($C_1$-$C_6$)alkyl, characterized in that, in a first method step a), a compound of the formula (I)

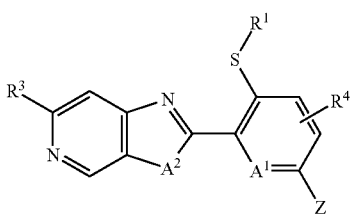

(I)

in which Z, $R^1$, $R^3$, $R^4$, $A^1$ and $A^2$ are each as defined above, is reacted with an organozinc base of the structure (NR$^a$R$^b$)—Zn—R$^c$ or (NR$^a$R$^b$)$_2$—Zn, in which $R^c$ is halogen or —O-pivaloyl and $R^a$ and $R^b$ together form a —(CH$_2$)$_4$—, —(CH$_2$)$_5$— or —(CH$_2$)$_2$O(CH$_2$)$_2$— group, where each of these groups may optionally be substituted by 1, 2, 3 or 4 $R^d$ radicals and $R^d$ is selected from the group consisting of methyl, ethyl, n-propyl and isopropyl, to give a compound of the formula (IVa) or the formula (IVb),

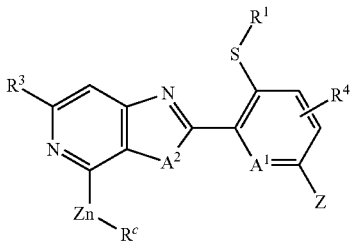

(IVa)

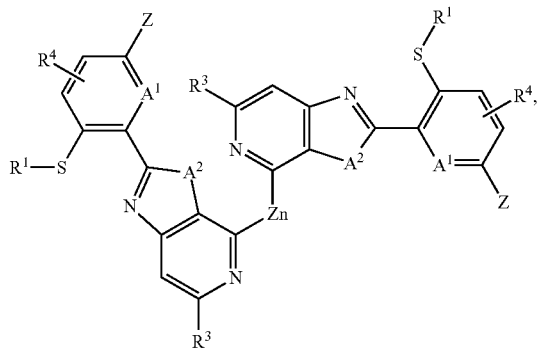

(IVb)

in which Z, $R^1$, $R^3$, $R^4$, $R^c$, $A^1$ and $A^2$ are each as defined above, and this compound of the formula (IVa) or (IVb) is reacted in a second method step b) with a compound of the structure Q-V, in which V is halogen and Q has the abovementioned definition, to give the compound of the formula (II).

DETAILED DESCRIPTION OF A PREFERRED EMBODIMENT

The compound Q-V, as apparent from the definitions of Q and V, is an interhalogen compound, preferably elemental halogen. Q and V need not necessarily be the same halogen. For example, Q may be iodine or bromine and V may be chlorine, bromine or iodine. Preferably, the compound Q-V, however, is an elemental halogen, especially $F_2$, $Cl_2$, $Br_2$ or $I_2$. Particular preference is given to $I_2$ or $Br_2$, very particular preference to $I_2$.

The radicals Z and Q are preferably different halogens, Z particularly preferably being fluorine, chlorine or bromine and in the case that Z is fluorine, Q is iodine, bromine or chlorine or
Z is chlorine, Q is iodine or bromine or
Z is bromine, Q is iodine.

The compounds of the formula (IVa) and (IVb) may also be present complexed with salts, where the salts are preferably alkali metal halides or alkaline earth metal halides, preferably lithium chloride and/or magnesium chloride and particularly preferably lithium chloride.

Preferred and particularly preferred definitions of the Q, Z, $R^1$, $R^3$, $R^4$, $R^c$, $A^1$ and $A^2$ radicals included in the aforementioned formulae (I), (II), (IVa) and (IVb) of the method according to the invention are elucidated hereinafter, with more specific description of the organozinc base further down, and so the preferred configurations of the base are specified at that point.

(Configuration 2)

Q is preferably chlorine, iodine or bromine,
Z is preferably bromine, fluorine or chlorine,
$R^c$ is preferably —O-pivaloyl, chlorine, bromine or iodine,
$A^1$ is preferably nitrogen, =$N^+$—$O^-$ or =C—$R^5$,
$A^2$ is preferably —N—$R^6$ or oxygen,
$R^1$ is preferably ($C_1$-$C_4$)alkyl, ($C_1$-$C_4$)hydroxyalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyloxy-($C_1$-$C_4$)alkyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylamino, di($C_1$-$C_4$)alkylamino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulfonylamino, or is ($C_1$-$C_4$)alkyl, ($C_1$-$C_4$)alkoxy, ($C_2$-$C_4$)alkenyl, ($C_2$-$C_4$)alkynyl, ($C_3$-$C_6$)cycloalkyl, each of which is optionally mono- or disubstituted by identical or different substituents from the group consisting of aryl, hetaryl and heterocyclyl, where aryl, hetaryl or heterocyclyl may each optionally be mono- or disubstituted by identical or different substituents from the group consisting of halogen, cyano, carbamoyl, aminosulfonyl, ($C_1$-$C_4$)alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)alkylsulfimino, $R^3$ is preferably hydrogen, cyano, halogen, nitro, acetyl, hydroxyl, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano($C_3$-$C_8$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, aminothiocarbonyl, NHCO—($C_1$-$C_4$)alkyl (($C_1$-$C_4$)alkylcarbonylamino) or is phenyl or hetaryl, each of which is optionally mono- or disubstituted by identical or different substituents, where (in the case of hetaryl) at least one carbonyl group may optionally be present and where possible substituents in each case are as follows: cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl and di($C_1$-$C_4$)alkylaminosulfonyl, $R^4$ is preferably hydrogen, cyano, halogen, nitro, acetyl, hydroxyl, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano($C_3$-$C_8$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, aminothiocarbonyl, NHCO—($C_1$-$C_4$)alkyl (($C_1$-$C_4$)alkylcarbonylamino), is furthermore preferably phenyl or hetaryl, each of which is optionally mono- or disubstituted by identical or different substituents, where (in the case of hetaryl) at least one carbonyl group may optionally be present and where possible substituents in each case are as follows: cyano, halogen, nitro, acetyl, amino, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, NHCO—($C_1$-$C_4$)alkyl (($C_1$-$C_4$)alkylcarbonylamino), $R^5$ is preferably hydrogen, cyano, halogen, nitro, acetyl, hydroxyl, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, $(C_1-C_4)$alkoxyimino, $(C_1-C_4)$alkyl-$(C_1-C_4)$alkoxyimino, $(C_1-C_4)$haloalkyl-$(C_1-C_4)$alkoxyimino, $(C_1-C_4)$alkylthio, $(C_1-C_4)$haloalkylthio, $(C_1-C_4)$alkylthio-$(C_1-C_4)$alkyl, $(C_1-C_4)$alkylsulfinyl, $(C_1-C_4)$haloalkylsulfinyl, $(C_1-C_4)$alkylsulfinyl-$(C_1-C_4)$alkyl, $(C_1-C_4)$alkylsulfonyl, $(C_1-C_4)$haloalkylsulfonyl, $(C_1-C_4)$alkylsulfonyl-$(C_1-C_4)$alkyl, $(C_1-C_4)$alkylsulfonyloxy, $(C_1-C_4)$alkylcarbonyl, $(C_1-C_4)$haloalkylcarbonyl, aminocarbonyl, aminothiocarbonyl, $(C_1-C_4)$alkylaminocarbonyl, di$(C_1-C_4)$alkylaminocarbonyl, $(C_1-C_4)$alkylsulfonylamino, $(C_1-C_4)$alkylamino, di$(C_1-C_4)$alkylamino, aminosulfonyl, $(C_1-C_4)$alkylaminosulfonyl, di$(C_1-C_4)$alkylaminosulfonyl, aminothiocarbonyl, NHCO—$(C_1-C_4)$alkyl ($(C_1-C_4)$alkylcarbonylamino) and $R^6$ is preferably $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_1-C_4)$haloalkoxy-$(C_1-C_4)$alkyl, $(C_2-C_4)$alkenyl, $(C_2-C_4)$alkenyloxy-$(C_1-C_4)$-alkyl, $(C_2-C_4)$haloalkenyloxy-$(C_1-C_4)$alkyl, $(C_2-C_4)$haloalkenyl, $(C_2-C_4)$cyanoalkenyl, $(C_2-C_4)$alkynyl, $(C_2-C_4)$alkynyloxy-$(C_1-C_4)$alkyl, $(C_2-C_4)$haloalkynyl, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkylthio-$(C_1-C_4)$alkyl, $(C_1-C_4)$haloalkylthio-$(C_1-C_4)$alkyl, $(C_1-C_4)$alkylsulfinyl-$(C_1-C_4)$alkyl, $(C_1-C_4)$haloalkylsulfinyl-$(C_1-C_4)$alkyl, $(C_1-C_4)$alkylsulfonyl-$(C_1-C_4)$alkyl, $(C_1-C_4)$haloalkylsulfonyl-$(C_1-C_4)$alkyl, $(C_1-C_4)$alkoxy-$(C_1-C_4)$alkylthio-$(C_1-C_4)$alkyl or $(C_1-C_4)$alkylcarbonyl-$(C_1-C_4)$alkyl.

(Configuration 3)

Q is particularly preferably chlorine, iodine or bromine,

Z is particularly preferably bromine, fluorine or chlorine, $R^c$ is particularly preferably —O-pivaloyl, chlorine, bromine or iodine, $A^1$ is particularly preferably nitrogen or =C—$R^5$, $A^2$ is particularly preferably —N—$R^6$, $R^1$ is particularly preferably $(C_1-C_4)$alkyl, $(C_1-C_4)$hydroxyalkyl, $(C_1-C_4)$haloalkyl, $(C_2-C_4)$alkenyl, $(C_2-C_4)$haloalkenyl, $(C_2-C_4)$alkynyl, $(C_2-C_4)$haloalkynyl, $(C_3-C_6)$cycloalkyl, $(C_1-C_4)$alkylthio-$(C_1-C_4)$alkyl, $(C_1-C_4)$alkylsulfinyl-$(C_1-C_4)$alkyl or $(C_1-C_4)$alkylsulfonyl-$(C_1-C_4)$alkyl, $R^3$ is particularly preferably hydrogen, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl or $(C_1-C_4)$haloalkylsulfonyl, $R^4$ is particularly preferably hydrogen, cyano, halogen, nitro, hydroxyl, amino, SCN, tri$(C_1-C_4)$alkylsilyl, $(C_3-C_6)$cycloalkyl, cyano$(C_3-C_8)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$cyanoalkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di$(C_1-C_4)$alkylaminocarbonyl, $(C_1-C_4)$alkylsulfonylamino, $(C_1-C_4)$alkylamino, di$(C_1-C_4)$alkylamino, aminosulfonyl, $(C_1-C_4)$alkylaminosulfonyl, di$(C_1-C_4)$alkylaminosulfonyl, NHCO—$(C_1-C_4)$alkyl ($(C_1-C_4)$alkylcarbonylamino), is furthermore particularly preferably phenyl or hetaryl, each of which is optionally mono- or disubstituted by identical or different substituents, where (in the case of hetaryl) at least one carbonyl group may optionally be present and where possible substituents in each case are as follows: cyano, halogen, $(C_3-C_6)$cycloalkyl, $(C_3-C_6)$cycloalkyl-$(C_3-C_6)$cycloalkyl, $(C_1-C_4)$alkyl-$(C_3-C_6)$cycloalkyl, halo$(C_3-C_6)$cycloalkyl, $(C_1-C_4)$alkyl, $(C_1-C_4)$haloalkyl, $(C_1-C_4)$cyanoalkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_1-C_4)$alkoxy, $(C_1-C_4)$haloalkoxy, $(C_1-C_4)$alkylhydroxyimino, $(C_1-C_4)$alkoxyimino, $(C_1-C_4)$alkyl-$(C_1-C_4)$alkoxyimino, $(C_1-C_4)$alkylthio, $(C_1-C_4)$haloalkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, $(C_1-C_4)$alkylsulfonyloxy, $(C_1-C_4)$alkylcarbonyl, $(C_1-C_4)$haloalkylcarbonyl, aminocarbonyl, $(C_1-C_4)$alkylaminocarbonyl, di$(C_1-C_4)$alkylaminocarbonyl, $(C_1-C_4)$alkylsulfonylamino, $(C_1-C_4)$alkylamino, di$(C_1-C_4)$alkylamino, aminosulfonyl, $(C_1-C_4)$alkylaminosulfonyl, di$(C_1-C_4)$alkylaminosulfonyl, NHCO—$(C_1-C_4)$alkyl ($(C_1-C_4)$alkylcarbonylamino), $R^5$ is particularly preferably hydrogen, halogen, cyano or $(C_1-C_4)$alkyl and $R^6$ is particularly preferably $(C_1-C_4)$alkyl or $(C_1-C_4)$alkoxy-$(C_1-C_4)$alkyl.

(Configuration 4)

Q is especially preferably iodine or bromine,

Z is especially preferably bromine or chlorine, $R^c$ is especially preferably chlorine, bromine or iodine, $A^1$ is especially preferably nitrogen or =C—$R^5$, $A^2$ is especially preferably —N—$R^6$, $R^1$ is especially preferably methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl, $R^3$ is especially preferably fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulfonyl or trifluoromethylsulfinyl, $R^4$ is especially preferably hydrogen, cyano, halogen, $(C_1-C_4)$alkyl, $(C_1-C_4)$haloalkyl, $(C_1-C_4)$haloalkoxy, $(C_1-C_4)$alkylthio, $(C_1-C_4)$alkylsulfinyl, $(C_1-C_4)$alkylsulfonyl, $(C_1-C_4)$haloalkylthio, $(C_1-C_4)$haloalkylsulfinyl, $(C_1-C_4)$haloalkylsulfonyl or NHCO—$(C_1-C_4)$alkyl ($(C_1-C_4)$alkylcarbonylamino), $R^5$ is especially preferably hydrogen, fluorine, chlorine, bromine or cyano and $R^6$ is especially preferably methyl, ethyl, isopropyl, methoxymethyl or methoxyethyl.

(Configuration 5)

Q is particularly iodine or bromine,

Z is particularly bromine or chlorine, $R^c$ is particularly chlorine or bromine, $A^1$ is particularly nitrogen, $A^2$ is particularly —N—$R^6$, $R^1$ is particularly methyl, ethyl, n-propyl, isopropyl or cyclopropyl, $R^3$ is particularly trifluoromethyl or pentafluoroethyl, $R^4$ is particularly hydrogen and $R^6$ is particularly methyl.

(Configuration 6)
Q is especially iodine or bromine,
Z is especially bromine or chlorine,
$R^c$ is especially chlorine,
$A^1$ is especially nitrogen,
$A^2$ is especially —N—$R^6$,
$R^1$ is especially ethyl,
$R^3$ is especially trifluoromethyl,
$R^4$ is especially hydrogen and
$R^6$ is especially methyl.

The radical definitions and elucidations given above apply both to the end products and intermediates and to the starting materials in a corresponding manner. These radical definitions can be combined with one another as desired, i.e. including combinations between the respective preferred ranges.

By definition, unless stated otherwise, halogen is selected from the group of fluorine, chlorine, bromine and iodine, preferably in turn from the group of fluorine, chlorine and bromine.

In the context of the present invention, unless defined differently elsewhere, the term "alkyl", either on its own or else in combination with further terms, for example haloalkyl, is understood to mean a radical of a saturated, aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl.

The term "alkoxy", either on its own or else in combination with further terms, for example haloalkoxy, is understood in the present case to mean an O-alkyl radical, where the term "alkyl" is as defined above.

According to the invention, unless defined differently elsewhere, the term "aryl" is understood to mean an aromatic radical having 6 to 14 carbon atoms, preferably phenyl, naphthyl, anthryl or phenanthrenyl, more preferably phenyl.

Unless defined differently elsewhere, the term "arylalkyl" is understood to mean a combination of the radicals "aryl" and "alkyl" defined in accordance with the invention, where the radical is generally bonded via the alkyl group; examples of these are benzyl, phenylethyl or α-methylbenzyl, particular preference being given to benzyl.

Unless defined differently elsewhere, "hetaryl" or "heteroaromatic ring" denotes a mono-, bi- or tricyclic heterocyclic group composed of carbon atoms and at least one heteroatom, where at least one ring is aromatic. Preferably, the hetaryl group contains 3, 4, 5, 6, 7 or 8 carbon atoms. Particular preference is given here to monocyclic groups of 3, 4, 5, 6, 7 or 8 carbon atoms and at least one heteroatom. The hetaryl group is particularly preferably selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl, imidazopyridinyl and indolizinyl.

Halogen-substituted radicals, for example haloalkyl, are mono- or polyhalogenated, up to the maximum number of possible substituents. In the case of polyhalogenation, the halogen atoms may be identical or different. Unless stated otherwise, optionally substituted radicals may be mono- or polysubstituted, where the substituents in the case of polysubstitutions may be the same or different.

Advantageously, the halogenated imidazopyridine derivatives of the formula (II) can be prepared by the method according to the invention with good yields and in high purity. Because of the very good functional group tolerance of zinc reagents, zinc bases are very attractive. Regio- and chemoselective metallations of imidazopyridines in the presence of stoichiometric amounts of selective bases are made possible, even at elevated temperatures, without aryne elimination taking place or sensitive functional groups being attacked. The zinc compound formed as intermediate can subsequently be scavenged with various electrophiles, as described by way of example in Organic Letters 2009 (11), p. 1837ff. These imidazopyridine derivatives having novel substitution can then be further reacted as valuable synthons.

The method according to the invention can be elucidated by the following scheme (I):

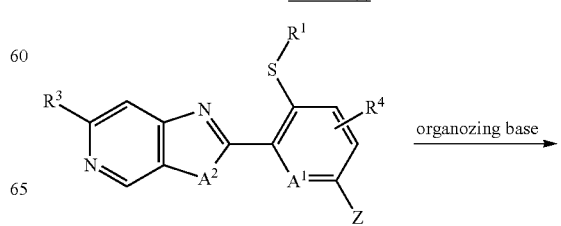

Scheme (I)

-continued

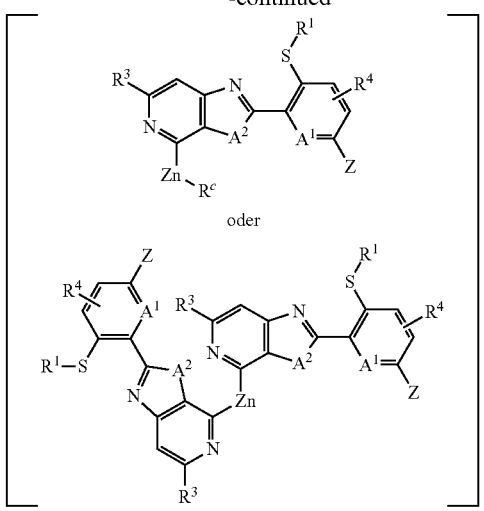

In this scheme, Q, V, Z, $R^1$, $R^3$, $R^4$, $R^c$, $A^1$ and $A^2$ are as defined above. The compounds shown in brackets are the intermediate (formula (IVa) or formula (IVb)) which is reacted further to give the compound of the formula (II). Accordingly, the method according to the invention can be divided into the two method steps a) and b), step a) being the conversion of the compound of the formula (I) to the respective intermediate and step b) being the further conversion of the intermediate to the compound of the formula (II).

General Definitions

In the context of the present invention, the term halogen, unless defined otherwise, encompasses those elements selected from the group consisting of fluorine, chlorine, bromine and iodine.

The term "halides" in connection with the present invention describes compounds between halogens and elements of other groups of the Periodic Table, which can give rise to halide salts (ionic compounds (salts) which consist of anions and cations because of the great difference in electronegativity between the elements involved and are held together by electrostatic interactions) or covalent halides (covalent compounds where the difference in electronegativity is not as great as in the aforementioned ionic compounds, but the bonds have charge polarity), depending on the nature of the chemical bond. Particular preference is given in accordance with the invention to halide salts.

The term "pivaloyl" in the context of the present invention describes the deprotonated radical of pivalic acid (IX) having the empirical formula $(CH_3)_3CCO_2H$.

(IX)

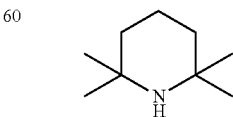

"O-pivaloyl" correspondingly means that the bond of the pivaloyl radical is via the deprotonated oxygen atom of the acid group.

Optionally substituted groups may be mono- or polysubstituted, where the substituents in the case of polysubstitutions may be the same or different.

Alkyl groups substituted by one or more halogen atoms (-Hal) are, for example, selected from trifluoromethyl ($CF_3$), difluoromethyl ($CHF_2$), $CF_3CH_2$, $ClCH_2$ or $CF_3CCl_2$.

Alkyl groups in the context of the present invention, unless defined otherwise, are straight-chain, branched or cyclic saturated hydrocarbyl groups.

The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

The conversion of the compounds of the formula (I) to compounds of the formula (IVa) or formula (IVb) in the first method step (step a)) is effected in the presence of an organozinc base of the structure $(NR^aR^b)$—Zn—$R^c$ or $(NR^aR^b)_2$—Zn, in which (configuration B-1)
$R^c$ is as defined above (configuration 1) (and is therefore halogen or —O-pivaloyl),
$R^a$ and $R^b$ together form a —$(CH_2)_4$—, —$(CH_2)_5$— or —$(CH_2)_2O(CH_2)_2$— group, where each of these groups may optionally be substituted by 1, 2, 3 or 4 $R^d$ radicals and
$R^d$ is selected from the group consisting of methyl, ethyl, n-propyl and isopropyl.

It is preferable that (configuration B-2)
$R^c$ is as defined above as preferred (configuration 2) (and is therefore —O-pivaloyl, chlorine, bromine or iodine),
$R^a$ and $R^b$ together form a —$(CH_2)$— group, where each of these groups may optionally be substituted by 1, 2, 3 or 4 $R^d$ radicals and
$R^d$ is selected from the group consisting of methyl and ethyl.

It is particularly preferable that (configuration B-3)
$R^c$ is as defined above as particularly preferred (configuration 6) (and is therefore chlorine) and
$R^a$ and $R^b$ together form a —$(CH_2)_5$— group substituted by 4 methyl groups.

The radical definitions given above can be combined with one another as desired, i.e. including combinations between the respective preferred ranges.

In a very particularly preferred configuration of the base according to the invention, the structural element $(NR^aR^b)$ is tetramethylpiperidine (TMP) of formula (V).

(V)

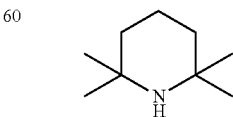

Organozinc bases most preferred in accordance with the invention are accordingly characterized in that zinc is bound to TMP, especially in the form of zinc halide and most preferably in the form of zinc chloride. Bases of this kind have the following structure of the formula (VI) (configuration B-4)

$$(TMP)_xZnCl_{2-x}, \quad (VI)$$

in which x is the number 1 or 2. Among these, preference is given in turn to bases with x=1 (configuration B-5) of formula (VII):

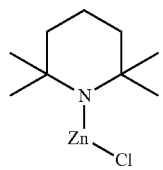

(VII)

In a further preferred embodiment of the method according to the invention, the organometallic base is present in conjunction with alkali metal halides or alkaline earth metal halides. This is especially true of bases of the formulae (VI) and (VII). Particularly preferred alkali metal halides or alkaline earth metal halides of this kind are lithium chloride and magnesium chloride, very particular preference being given to lithium chloride. Organometallic bases that are very particularly preferred in accordance with the invention are accordingly TMP ZnCl.LiCl or (TMP)₂Zn.2LiCl or (TMP)₂Zn.2LiCl 2 MgCl₂ (configuration B-6). Most preferred is TMP ZnCl.LiCl (VIII; configuration B-7).

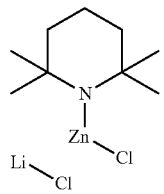

(VIII)

Specific combinations of compounds of the formulae (I), (II) and (IVa) or (IVb) with bases according to the invention are cited hereinafter by way of example in Table 1, these being employable in a method according to the invention. Since, in some configurations, the structural element $R^c$ is present both in the base according to the invention and in the compound of the formula (IVa), the narrowest definition applies to $R^c$ in each case.

TABLE 1

| Number | Compounds of the formulae (I), (II) and (IVa) or (IVb) | Base according to |
|---|---|---|
| 1 | Configuration 1 | Configuration B-1 |
| 2 | Configuration 1 | Configuration B-2 |
| 3 | Configuration 1 | Configuration B-3 |
| 4 | Configuration 1 | Configuration B-4 |
| 5 | Configuration 1 | Configuration B-5 |
| 6 | Configuration 1 | Configuration B-6 |
| 7 | Configuration 1 | Configuration B-7 |
| 8 | Configuration 2 | Configuration B-1 |
| 9 | Configuration 2 | Configuration B-2 |
| 10 | Configuration 2 | Configuration B-3 |
| 11 | Configuration 2 | Configuration B-4 |
| 12 | Configuration 2 | Configuration B-5 |
| 13 | Configuration 2 | Configuration B-6 |
| 14 | Configuration 2 | Configuration B-7 |
| 15 | Configuration 3 | Configuration B-1 |
| 16 | Configuration 3 | Configuration B-2 |
| 17 | Configuration 3 | Configuration B-3 |
| 18 | Configuration 3 | Configuration B-4 |
| 19 | Configuration 3 | Configuration B-5 |
| 20 | Configuration 3 | Configuration B-6 |
| 21 | Configuration 3 | Configuration B-7 |
| 22 | Configuration 4 | Configuration B-1 |
| 23 | Configuration 4 | Configuration B-2 |
| 24 | Configuration 4 | Configuration B-3 |
| 25 | Configuration 4 | Configuration B-4 |
| 26 | Configuration 4 | Configuration B-5 |
| 27 | Configuration 4 | Configuration B-6 |
| 28 | Configuration 4 | Configuration B-7 |
| 29 | Configuration 5 | Configuration B-1 |
| 30 | Configuration 5 | Configuration B-2 |
| 31 | Configuration 5 | Configuration B-3 |
| 32 | Configuration 5 | Configuration B-4 |
| 33 | Configuration 5 | Configuration B-5 |
| 34 | Configuration 5 | Configuration B-6 |
| 35 | Configuration 5 | Configuration B-7 |
| 36 | Configuration 6 | Configuration B-1 |
| 37 | Configuration 6 | Configuration B-2 |
| 38 | Configuration 6 | Configuration B-3 |
| 39 | Configuration 6 | Configuration B-4 |
| 40 | Configuration 6 | Configuration B-5 |
| 41 | Configuration 6 | Configuration B-6 |
| 42 | Configuration 6 | Configuration B-7 |

Preferably, the organometallic base is used in the method according to the invention in a total amount of 0.5 to 5 equivalents, preferably of 0.8 to 2 equivalents, further preferably of 1 to 1.5 equivalents and more preferably of 1.0 to 1.2 equivalents, based on the compound of the formula (I). One advantage of the method according to the invention in this regard is that the organometallic base can be used in virtually stoichiometric amounts.

Depending on whether the structural element ($NR^aR^b$) is present once or twice in the organozinc base used, intermediate compounds of the formula (IVa) or of the formula (IVb) are formed in method step a).

The conversion of the compounds of the formula (IVa) or (IVb) to compounds of the formula (II) in the second method step (step b)) is effected in the presence of a compound Q-V in which Q and V each have the definitions given above. Since both Q and V are halogen, the compound is an interhalogen compound. Q and V need not necessarily be the same halogen. For example, Q may be iodine or bromine and V may be chlorine, bromine or iodine. Preferably, the compound Q-V, however, is an elemental halogen, especially $F_2$, $Cl_2$, $Br_2$ or $I_2$. Particular preference is given to $I_2$ or $Br_2$, very particular preference to $I_2$.

Q-V is preferably selected such that the radicals Z and Q are different halogens, particularly preferably in the case that
Z is fluorine, Q is iodine, bromine or chlorine or
Z is chlorine, Q is iodine or bromine or
Z is bromine, Q is iodine.

Preferably, the compound Q-V is used in the method according to the invention in a total amount of 0.5 to 10.0 equivalents, preferably of 0.8 to 5 equivalents, further preferably of 1 to 2.5 equivalents and more preferably of 1.0 to 1.5 equivalents, based on the compound of the formula (I).

The conversion according to the invention of the compounds of the formula (I) to compounds of the formula (IVa) or (IVb) and further to compounds of the formula (II) is preferably effected in the presence of an organic solvent in each case. Useful solvents in principle include all organic solvents which are inert under the reaction conditions employed and in which the compounds to be converted have adequate solubility. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the solvents mentioned above such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tert-amyl methyl ether (TAME), 2-methyl-THF, toluene and 4-methoxybenzene.

Particularly preferred solvents are THF and N,N-dimethylformamide (DMF), very particular preference being given to THF.

The solvent may also be degassed (oxygen-free).

Preference is given to using the same solvent for both method steps a) and b). Alternative configurations of the invention in which different solvents are used for method steps a) and b) are likewise possible, however, in which case the solvents are likewise preferably selected from the aforementioned solvents, and the respective solvents specified as being preferred, particularly preferred and especially preferred are applicable to the respective method step a) or b).

The reaction of method step a) is particularly good at elevated temperatures. The reaction in method step a) is therefore generally conducted at a temperature between 0° C. and 110° C. and with increasing preference between 20° C. and 100° C., between 30° C. and 95° C., between 40° C. and 90° C., between 60° C. and 85° C., and most preferably between 70° C. and 85° C., for example at 80° C.

The reaction in method step b) is generally conducted at a temperature between 0° C. and 80° C. and with increasing preference between 10° C. and 70° C., between 15° C. and 60° C., between 20° C. and 50° C., between 20° C. and 40° C., and most preferably between 20° C. and 35° C., for example at room temperature or 25° C.

The reaction is typically conducted at standard pressure, but can also be conducted at elevated or reduced pressure.

The desired compounds of the formula (II) can be isolated, for example, by aqueous workup in the presence of saturated ammonium chloride or sodium thiosulfate solutions and/or subsequent chromatography. Such methods are known to those skilled in the art and also include crystallization from an organic solvent or solvent mixture.

A particularly preferred embodiment of the method according to the invention can be elucidated with reference to the following scheme (II):

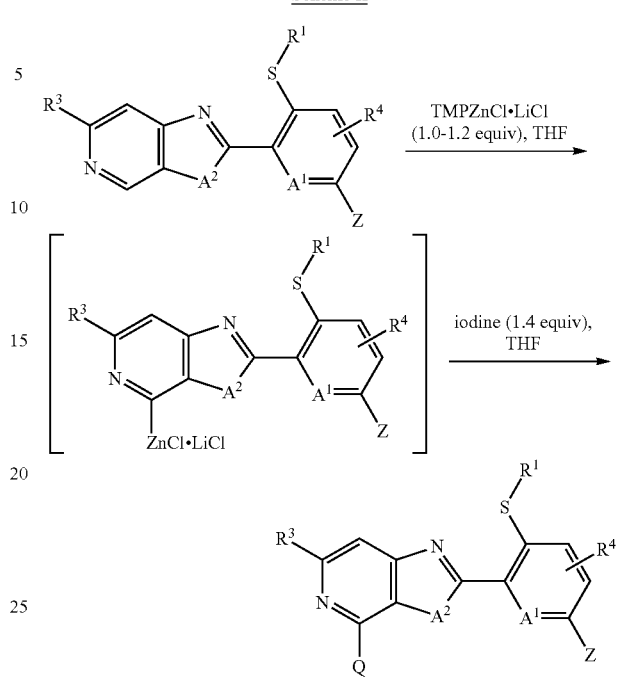

Scheme II

In this scheme, Q, V, Z, $R^1$, $R^3$, $R^4$, $A^1$ and $A^2$ are as defined above. The compound shown in brackets represents the corresponding intermediate of the formula (IVa) which is further reacted to give the product, a compound of the formula (II). Both reactions take place in THF as solvent. "Equiv" refers to the amount of equivalents of TMPZnCl·LiCl or iodine ($I_2$) used.

In a specific embodiment of the invention, the compounds of the formula (II) are reacted further in a third step c) to give compounds of the formula (III)

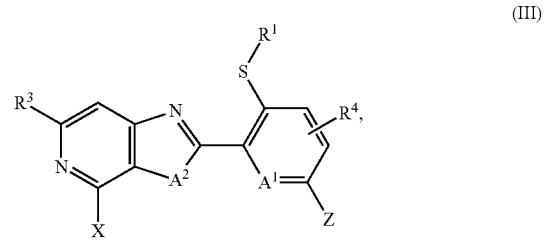

(III)

in which Z, $R^1$, $R^3$, $R^4$, $A^1$ and $A^2$ have the abovementioned definitions and preferred ranges according to any of configurations 1 to 6 and (Configuration (X-1))

X is cyano, carboxyl, halogen, nitro, acetyl, hydroxyl, amino, SCN, tri($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl ($C_1$-$C_6$)alkoxy, ($C_1$-$C_6$)haloalkoxy, ($C_1$-$C_6$)cyanoalkoxy, ($C_1$-$C_6$)alkoxycarbonyl- ($C_1$-$C_6$)alkoxy, ($C_1$-$C_6$)alkoxy-($C_1$-$C_6$)alkoxy, ($C_1$-$C_6$)alkoxyimino, —N=C(H)—O($C_1$-$C_6$)alkyl, —C(H)=N—O($C_1$-$C_6$)alkyl, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, ($C_1$-$C_6$)alkylcarbamoyl (including —NHCOO($C_1$-$C_6$)alkyl, —N($C_1$-$C_6$)alkylCOO($C_1$-$C_6$)alkyl, —OCONH($C_1$-$C_6$)alkyl or —OCON($C_1$-$C_6$)dialkyl), ($C_1$-$C_6$)alkylcarbonylamino ((($C_1$-$C_6$)alkylCONH), ($C_1$-$C_6$)alkylurea (including —NHCONH($C_1$-$C_6$)alkyl, and —NHCON($C_1$-$C_6$)dialkyl) or is a saturated, partially saturated or heteroaromatic ring which is optionally mono- or polysubstituted by identical or different substituents and in which at least one carbon atom is replaced by a heteroatom, or is an aromatic ring which is mono- or polysubstituted by identical or different substituents, where at least one carbonyl group may optionally be present in each case and where possible substituents in each case are as follows: cyano, carboxyl, halogen, nitro, acetyl, hydroxyl, amino, SCN, tri($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkoxyimino, —N=C(H)—O($C_1$-$C_6$)alkyl, —C(H)=N—O($C_1$-$C_6$)alkyl, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino or ($C_1$-$C_6$)alkylcarbonylamino.

Preference is given to compounds of the formula (III) in which Z, $R^1$, $R^3$, $R^4$, $A^1$ and $A^2$ have the abovementioned definitions and preferred ranges according to any of configurations 1 to 6 and (Configuration (X-2))

X is preferably cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkoxyimino, —N=C(H)—O($C_1$-$C_4$)alkyl, —C(H)=N—O($C_1$-$C_4$)alkyl, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, ($C_1$-$C_4$)alkylcarbamoyl (including —NHCOO($C_1$-$C_4$)alkyl, —N($C_1$-$C_4$)alkylCOO($C_1$-$C_4$)alkyl, —OCONH($C_1$-$C_4$)alkyl or —OCON($C_1$-$C_4$)dialkyl), ($C_1$-$C_4$)alkylcarbonylamino ((($C_1$-$C_4$)alkylCONH) or ($C_1$-$C_4$)alkylurea (including —NHCONH($C_1$-$C_6$)alkyl and —NHCON($C_1$-$C_6$)dialkyl).

Particular preference is given to compounds of the formula (III) in which Z, $R^1$, $R^3$, $R^4$, $A^1$ and $A^2$ have the abovementioned definitions and preferred ranges according to any of configurations 1 to 6 and (Configuration (X-3))

X is cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)cyanoalkoxy or ($C_1$-$C_4$)alkoxy-($C_1$-$C_4$)alkoxy.

Very particular preference is given to compounds of the formula (III) in which Z, $R^1$, $R^3$, $R^4$, $A^1$ and $A^2$ have the abovementioned definitions and preferred ranges according to any of configurations 1 to 6 and (Configuration (X-4))

X is cyano, halogen, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, (($C_1$-$C_4$)alkoxy or ($C_1$-$C_4$)cyanoalkoxy.

Emphasis is given to compounds of the formula (III) in which Z, $R^1$, $R^3$, $R^4$, $A^1$ and $A^2$ have the abovementioned definitions and preferred ranges according to any of configurations 1 to 6 and (Configuration (X-5-1))

X is cyano, halogen, ($C_1$-$C_4$)alkyl, ($C_3$-$C_6$)cycloalkyl, ($C_2$-$C_4$)alkynyl, ($C_2$-$C_4$)alkenyl, ($C_3$-$C_6$)cyanocycloalkyl or ($C_3$-$C_6$)halocycloalkyl.

Emphasis is further given to compounds of the formula (III) in which Z, $R^1$, $R^3$, $R^4$, $A^1$ and $A^2$ have the abovementioned definitions and preferred ranges according to any of configurations 1 to 6 and
(Configuration (X-5-2))

X is cyano, halogen, ($C_1$-$C_4$)alkyl, ($C_3$-$C_6$)cycloalkyl, ($C_3$-$C_6$)cyanocycloalkyl or ($C_3$-$C_6$)halocycloalkyl.

Particular preference is given to compounds of the formula (III) in which Z, $R^1$, $R^3$, $R^4$, $A^1$ and $A^2$ have the abovementioned definitions and preferred ranges according to any of configurations 1 to 6 and
(Configuration (X-6-1))

X is cyano, methyl, ethyl, vinyl, ethynyl or chlorine.

Particular preference is further given to compounds of the formula (III) in which Z, $R^1$, $R^3$, $R^4$, $A^1$ and $A^2$ have the abovementioned definitions and preferred ranges according to any of configurations 1 to 6 and
(Configuration (X-6-2))

X is cyano, methyl or chlorine.

The conversion of the compounds of the formula (II) to compounds of the formula (III) (step c), i.e. the introduction of the radical X, is preferably carried out by coupling, particularly preferably by a cross-coupling or a metal-catalysed reaction.

The compounds of the formula (II) are reacted in this case preferably with organozinc reagents in the presence of a catalyst or with metal salts, particularly copper salts.

Reactions of this kind are described, for example, in Chemistry, A European Journal 15 (2009) (organozinc reagents) and Organic Letters, 13 (2011), 648-651 or Organic & Biomolecular Chemistry, 7 (2009), 1043-1052 (metal salts).

The conversion according to the invention of the compounds of the formula (II) to compounds of the formula (III) is preferably effected in the presence of an organic solvent in each case. Useful solvents in principle include all organic solvents which are inert under the reaction conditions employed and in which the compounds to be converted have adequate solubility. The solvent may also be degassed (oxygen-free).

Preferably, the organozinc compound or the metal salt in the method according to the invention is used in a total amount of 0.5 to 10 equivalents, preferably 0.8 to 5 equivalents, particularly preferably 1 to 3.0 equivalents, based on the compound of the formula (II).

The reaction in method step c) is generally conducted at a temperature between 0° C. and 110° C. and with increasing preference between 10° C. and 100° C., between 20° C. and 90° C., and most preferably between 30° C. and 90° C.

The reaction is typically conducted at standard pressure, but can also be conducted at elevated or reduced pressure.
Introduction of the Radical X Via Organozinc Reagents:

The compounds of the formula (III) can be prepared by Negishi cross-coupling using organozinc reagents in the presence of a catalyst, as described in Chemistry, A European Journal 15 (2009), 1468-1477.

Preferably, the organozinc compound is used in the method according to the invention in a total amount of 0.5 to 10 equivalents, preferably of 0.8 to 5 equivalents, further preferably of 1.0 to 3.5 equivalents and more preferably of 1.5 to 3.0 equivalents, based on the compound of the formula (II). An advantage of the method according to the invention in this regard is that the organozinc reagent is commercially available and may be used in a highly regio- and chemoselective manner.

Preferred zinc reagents are those of the formula YZnCl or YZnBr, particular preference being given to YZnCl, where Configuration (Y-1)

Y is ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$) cyanocycloalkyl, ($C_3$-$C_6$)cycloalkyl-($C_3$-$C_6$)cycloalkyl, (($C_1$-$C_4$)alkyl-($C_3$-$C_6$)cycloalkyl
and the reagents may also be present complexed with lithium chloride and/or magnesium chloride.

With particular preference (configuration Y-2)

Y is ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)alkynyl, ($C_2$-$C_4$)haloalkenyl, ($C_2$-$C_4$) cyanoalkenyl, ($C_3$-$C_6$)cycloalkyl, ($C_3$-$C_6$)halocycloalkyl, ($C_3$-$C_6$)cyanocycloalkyl or ($C_1$-$C_4$)alkyl-($C_3$-$C_6$)cycloalkyl.

With very particular preference (configuration Y-3), Y is ($C_1$-$C_4$)alkyl, ($C_2$-$C_4$)alkenyl, ($C_2$-$C_4$)alkynyl or ($C_3$-$C_6$) cycloalkyl.

In particular (configuration Y-4), Y is methyl, ethyl, propyl, butyl, vinyl, ethynyl or cyclopropyl.

The reaction with organozinc reagents in method step c) is further preferably carried out in the presence of a catalyst. Preferably, the catalyst is a palladium compound or a nickel compound. More preferably, the catalyst is a palladium compound. It is especially preferably tetrakis(triphenylphosphine)palladium(0), abbreviated to Pd(PPh$_3$)$_4$, of the formula (XI).

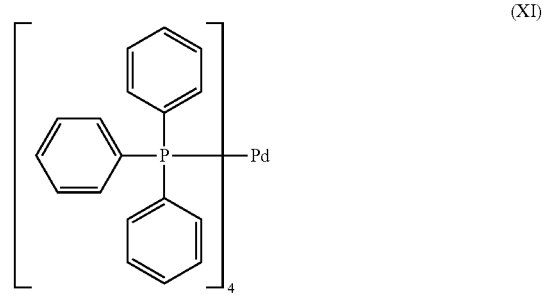

(XI)

In the reaction with organozinc reagents in step c), 2.5 to 25 mol % and preferably 5 to 20 mol % catalyst is typically used.

The conversion according to the invention of the compounds of the formula (II) to compounds of the formula (III) using organozinc reagents is preferably effected in the presence of an organic solvent in each case. Suitable solvents especially include: tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the aforementioned solvents such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are THF, N,N-dimethylformamide (DMF), 1,4-dioxane, diglyme, methyl tert-butyl ether (MTBE), tert-amyl methyl ether (TAME), 2-methyl-THF, toluene and 4-methoxybenzene.

Particularly preferred solvents are THF and N,N-dimethylformamide (DMF), very particular preference being given to THF.

The reaction with organozinc reagents in method step c) is generally conducted at a temperature between 0° C. and 80° C. and with increasing preference between 5° C. and 75° C., between 10° C. and 70° C., between 20° C. and 60° C., between 25° C. and 65° C., and most preferably between 30° C. and 50° C., for example at 40° C.

The reaction with organozinc reagents in method step c) is generally carried out with a reaction time of between 0.5 and 10 h and with increasing preference of between 1 and 7 h, between 1.5 and 6 h and especially preferably between 2 and 5 h, for example 3 h. The desired compounds of the formula (III) can be isolated, for example, by aqueous workup in the presence of saturated ammonium chloride or sodium thiosulfate solutions and/or subsequent chromatography. Such processes are known to those skilled in the art and also include crystallization from an organic solvent or solvent mixture.

Introduction of the Radical X Via Metal Salts:

The compounds of the formula (III) can be prepared by Negishi cross-coupling using metal salts, as described in Organic Letters, 13 (2011), 648-651 or Organic & Biomolecular Chemistry, 7 (2009), 1043-1052.

Preferably, the metal salts are used in the method according to the invention in a total amount of 0.5 to 10 equivalents, preferably of 0.8 to 5 equivalents, further preferably of 1 to 2.5 equivalents and more preferably of 1.0 to 1.5 equivalents, based on the compound of the formula (II). An advantage of the method according to the invention in this regard is that the metal salts are commercially available and may be used in a highly regio- and chemoselective manner. In addition, the addition of a catalyst may be omitted.

Preferred metal salts are copper salts and particular preference is given to CuCN or CuCl.

The conversion according to the invention of the compounds of the formula (II) to compounds of the formula (III) using metal salts is preferably effected in the presence of an organic solvent in each case. Suitable solvents especially include: pyridine, tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, ethylene carbonate, propylene carbonate, N,N-dimethylacetamide, N,N-dimethylformamide (DMF), N-methylpyrrolidone (NMP), N-ethyl-2-pyrrolidone (NEP), N-butyl-2-pyrrolidone (NBP); N,N'-dimethylpropyleneurea (DMPU), halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; 4-methoxybenzene, fluorinated aliphatics and aromatics, such as trichlorotrifluoroethane, benzotrifluoride and 4-chlorobenzotrifluoride. It is also possible to use solvent mixtures, preferably mixtures of the aforementioned solvents such as tetrahydrofuran (THF), 1,4-dioxane, diethyl ether, diglyme, methyl tert-butyl ether (MTBE), tert-amyl methyl ether (TAME), 2-methyl-THF, toluene, xylenes, mesitylene, dimethylformamide (DMF).

Preferred solvents are pyridine, THF, dioxane and DMF.

Particularly preferred solvents are pyridine, THF and DMF, very particular preference being given to pyridine.

The reaction with metal salts in method step c) is generally conducted at a temperature between 0° C. and 120° C. and with increasing preference between 30° C. and 110° C., between 40° C. and 100° C., between 50° C. and 90° C., between 60° C. and 95° C., and most preferably between 70° C. and 90° C., for example at 80° C.

The reaction with metal salts in method step c) is generally carried out with a reaction time of between 1 and 8 and with increasing preference of between 2 and 7, between 2.5 and 7.5 and especially preferably between 3 h and 6 h, for example 5 h. The desired compounds of the formula (III) can be isolated, for example, by aqueous workup in the presence of saturated ammonium chloride or sodium thiosulfate solutions and/or subsequent chromatography. Such processes are known to those skilled in the art and also include crystallization from an organic solvent or solvent mixture.

The present invention further provides compounds of the formula (IVa)

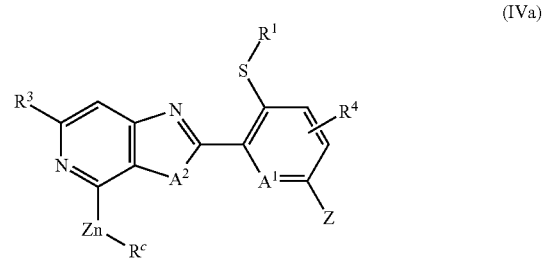

(IVa)

in which Z, $R^1$, $R^3$, $R^4$, $R^c$, $A^1$ and $A^2$ have the abovementioned definitions and preferred configurations according to any of configurations 1 to 6.

The compounds of the formula (IVa) may also be present complexed with salts, where the salts are preferably alkali metal halides or alkaline earth metal halides, preferably lithium chloride and/or magnesium chloride and particularly preferably lithium chloride.

Among the compounds of the formula (IVa), the following compounds are especially preferred, in which the respective compound can be present alone or as a lithium chloride complex:

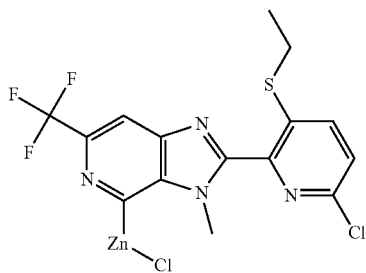

chloro{2-[6-chloro-3-(ethylsulfanyl)pyridin-2-yl]-3-methyl-6-(trifluoromethyl)-3H-imidazo[4,5-c]pyridin-4-yl}zinc

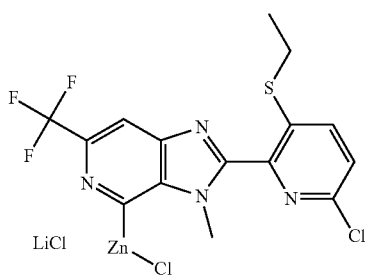

chloro{2-[6-chloro-3-(ethylsulfanyl)pyridin-2-yl]-3-methyl-6-(trifluoromethyl)-3H-imidazo[4,5-c]pyridin-4-yl}zinc lithium chloride complex

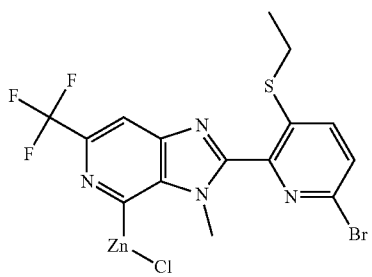

{2-[6-chloro-3-(ethylsulfanyl)pyridin-2-yl]-3-methyl-6-(trifluoromethyl)-3H-imidazo[4,5-c]pyridin-4-yl}(chloro)zinc

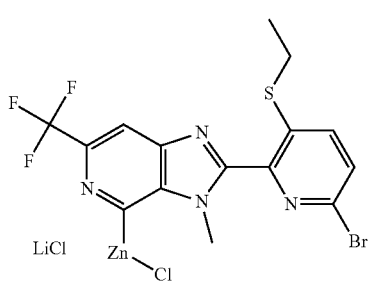

{2-[6-chloro-3-(ethylsulfanyl)pyridin-2-yl]-3-methyl-6-(trifluoromethyl)-3H-imidazo[4,5-c]pyridin-4-yl}(chloro)zinc lithium chloride complex The present invention further provides compounds of the formula (IVb)

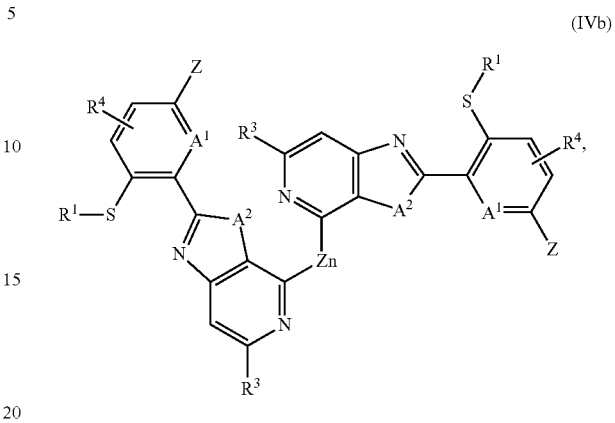

in which Z, $R^1$, $R^3$, $R^4$, $A^1$ and $A^2$ have the abovementioned definitions and preferred configurations.

The compounds of the formula (IVb) may also be present complexed with salts, where the salts are preferably alkali metal halides or alkaline earth metal halides, preferably lithium chloride and/or magnesium chloride as in structure (IVb-1) or (IVb-2) and particularly preferably lithium chloride (structure (IVb-1).

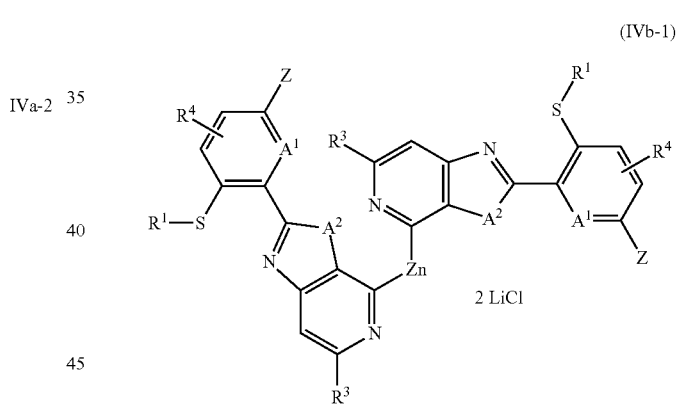

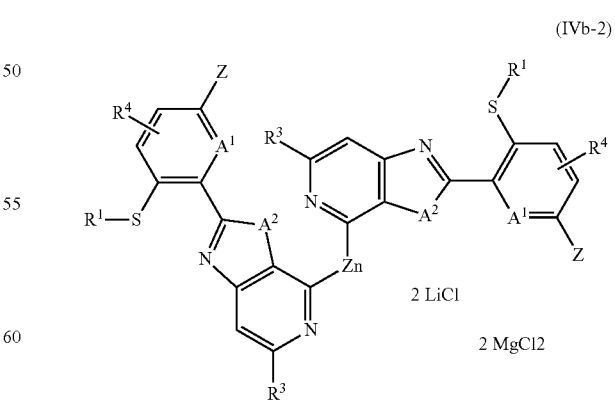

Z, $R^1$, $R^3$, $R^4$, $A^1$ and $A^2$ in formula (IVb-1) and (IVb-2) have the abovementioned definitions and preferred configurations.

The present invention further provides compounds of the formula (II)

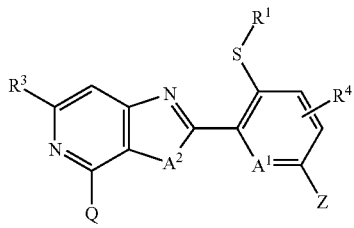

(II)

in which
Q, Z, $R^1$, $R^3$, $R^4$, $A^1$ and $A^2$ have the abovementioned definitions and preferred configurations.

Among the compounds of the formula (II), the following compounds are especially preferred:

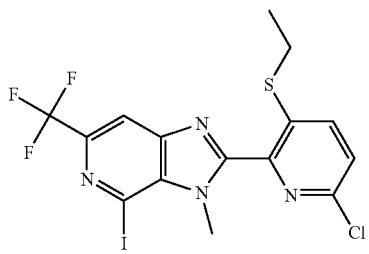 [SMILES: CCSc1ccc(Cl)nc1-c1nc2cc(C(F)(F)F)nc(I)c2n1C]

((II-1), 2-[6-chloro-3-(ethylsulfanyl)pyridin-2-yl]-4-iodo-3-methyl-6-(trifluoromethyl)-3H-imidazo[4,5-c]pyridine)

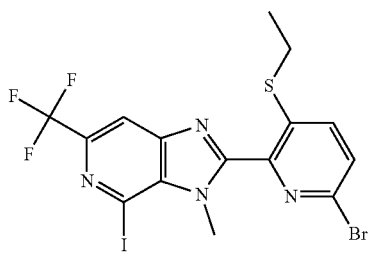

((II-2), 2-[6-bromo-3-(ethylsulfanyl)pyridin-2-yl]-4-iodo-3-methyl-6-(trifluoromethyl)-3H-imidazo[4,5-c]pyridine)

From these compounds of the formulae (II-1) to (II-2) arise the accompanying reactants (I-1 to I-2) of the formula (I) of the method according to the invention, which in each case are especially preferred compounds of the formula (I).

The present invention further provides compounds of the formula (III)

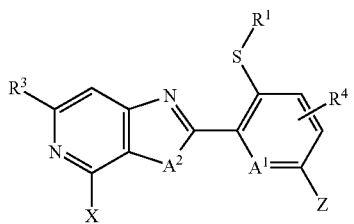

(III)

in which Z, $R^1$, $R^3$, $R^4$, $A^1$ and $A^2$ have the abovementioned definitions and preferred configurations according to any of configurations 1 to 6 and X is as defined above according to any of configurations X-1 to X-6.

Among the compounds of the formula (III), the following compounds are especially preferred:

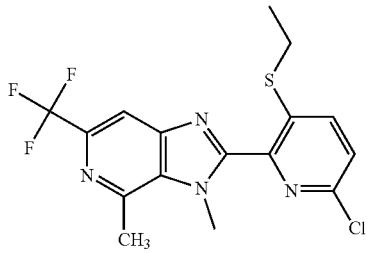 [SMILES: CCSc1ccc(Cl)nc1-c1nc2cc(C(F)(F)F)nc(C)c2n1C]

((III-1), 2-[6-chloro-3-(ethylsulfanyl)pyridin-2-yl]-3,4-dimethyl-6-(trifluoromethyl)-3H-imidazo[4,5-c]pyridine)

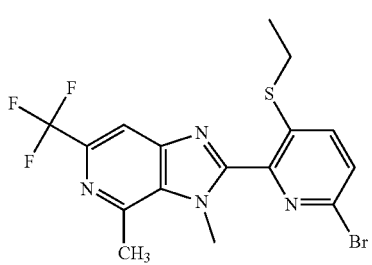

((III-2), 2-[6-bromo-3-(ethylsulfanyl)pyridin-2-yl]-3,4-dimethyl-6-(trifluoromethyl)-3H-imidazo[4,5-c]pyridine)

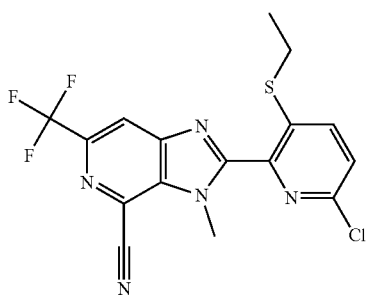 [SMILES: CCSc1ccc(Cl)nc1-c1nc2cc(C(F)(F)F)nc(C#N)c2n1C]

((III-3), 2-[6-chloro-3-(ethylsulfanyl)pyridin-2-yl]-3-methyl-6-(trifluoromethyl)-3H-imidazo[4,5-c]pyridine-4-carbonitrile)

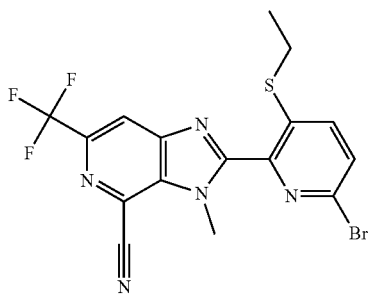

((III-4), 2-[6-bromo-3-(ethylsulfanyl)pyridin-2-yl]-3-methyl-6-(trifluoromethyl)-3H-imidazo[4,5-c]pyridine-4-carbonitrile)

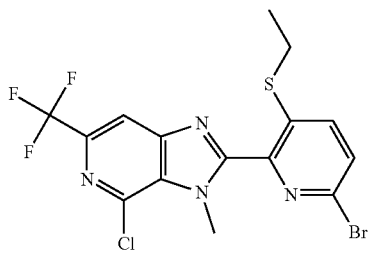

((III-5), 2-[6-bromo-3-(ethylsulfanyl)pyridin-2-yl]-4-chloro-3-methyl-6-(trifluoromethyl)-3H-imidazo[4,5-c]pyridine)

The present invention is elucidated in more detail by the examples which follow, although the examples should not be interpreted in such a manner that they restrict the invention.

Methods:

The log P values are measured according to EEC Directive 79/831 Annex V.A8 by HPLC (high-performance liquid chromatography) on a reversed-phase column (C 18). Temperature: 55° C.

The LC-MS determination in the acidic range is carried out at pH 2.7 using the mobile phases 0.1% aqueous formic acid and acetonitrile (contains 0.1% formic acid); linear gradient from 10% acetonitrile to 95% acetonitrile.

The LC-MS determination in the neutral range is carried out at pH 7.8 using the mobile phases 0.001 molar aqueous ammonium bicarbonate solution and acetonitrile; linear gradient from 10% acetonitrile to 95% acetonitrile.

Calibration is carried out using unbranched alkan-2-ones (having 3 to 16 carbon atoms) with known log P values (log P values determined on the basis of the retention times by linear interpolation between two successive alkanones).

The NMR data of selected examples are stated in classic form (δ values, multiplet splitting, number of hydrogen atoms).

In each case, the solvent in which the NMR spectrum was recorded is stated.

EXAMPLE 1

Synthesis of 2-[6-chloro-3-(ethylsulfanyl)pyridin-2-yl]-4-iodo-3-methyl-6-(trifluoromethyl)-3H-imidazo[4,5-c]pyridine

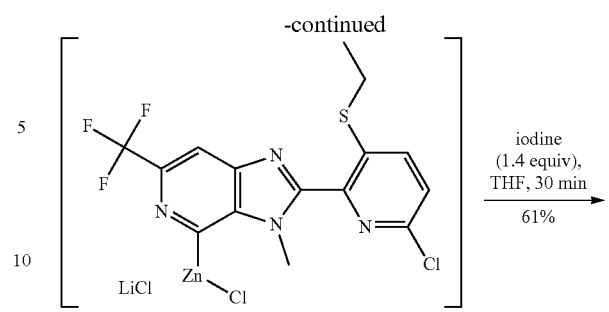

2-[6-Chloro-3-(ethylsulfanyl)pyridin-2-yl]-3-methyl-6-(trifluoromethyl)-3H-imidazo[4,5-c]pyridine (628 mg, 1.42 mmol) in anhydrous THF (3 ml) was initially charged in a dry, argon-filled 25-ml Schlenk flask, equipped with a magnetic stirrer bar and a septum. Zinc chloride-2,2,6,6-tetramethylpiperidin-1-ide lithium chloride complex (TMPZnCl·LiCl) (1.31M in THF, 1.2 ml, 1.56 mmol) was added dropwise and the mixture was stirred at 80° C. for 30 minutes. The reaction mixture was cooled to 25° C., then iodine (507 mg, 1.99 mmol) was added and the mixture was subsequently stirred at 25° C. for 30 minutes. Saturated aqueous ammonium chloride solution (25 ml) and sodium thiosulfate solution (25 ml) were added to the reaction mixture which was extracted with ethyl acetate (3*50 ml) and dried over anhydrous sodium sulfate. Following filtration, the solvent was removed under reduced pressure. The crude product was purified by chromatography, which gave 2-[6-chloro-3-(ethylsulfanyl)pyridin-2-yl]-4-iodo-3-methyl-6-(trifluoromethyl)-3H-imidazo[4,5-c]pyridine (464 mg, 61%) as a white solid.

HPLC-MS: log P=4.17; Mass (m/z): 499; $^1$H-NMR ($d_6$-DMSO): δ 8.32 (s, 1H), 8.16 (d, 1H), 7.80 (d, 1H), 4.06 (s, 3H), 3.05 (q, 2H), 1.20 (t, 3H).

EXAMPLE 2

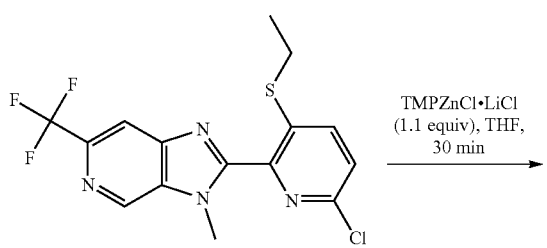

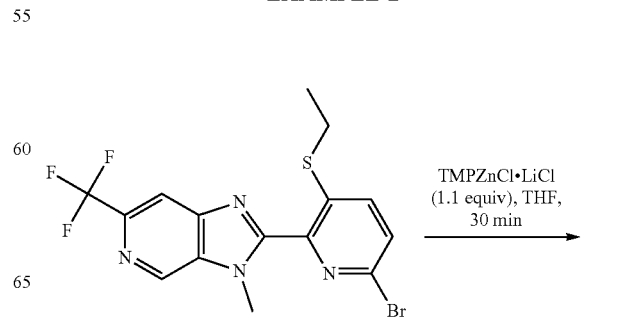

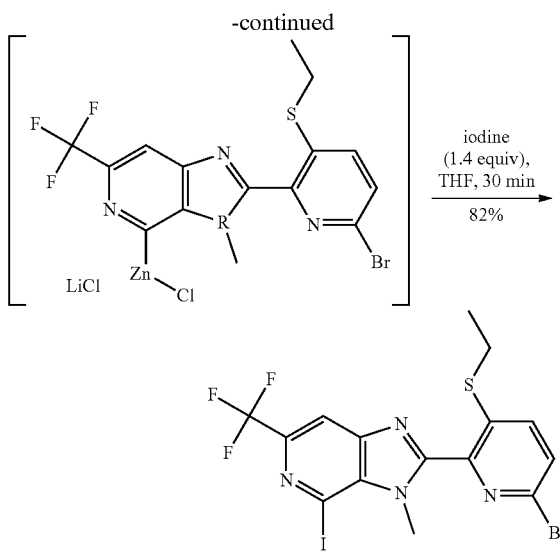

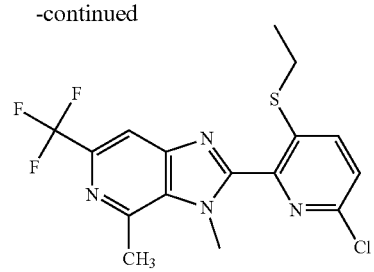

Synthesis of 2-[6-chloro-3-(ethylsulfanyl)pyridin-2-yl]-3,4-dimethyl-6-(trifluoromethyl)-3H-imidazo[4,5-c]pyridine To 2-[6-chloro-3-(ethylsulfanyl)pyridin-2-yl]-4-iodo-3-methyl-6-(trifluoromethyl)-3H-imidazo[4,5-c]pyridine (700 mg, 1.4 mmol), dissolved in THF (4 ml), was added MeZnCl (2.0 M in THF, 1.41 ml, 2.8 mmol) in the presence of tetrakis(triphenylphosphine)palladium(0) (163 mg, 0.14 mmol) at 40° C. under argon; this reaction solution was stirred for 3 hours. After customary workup by addition of saturated ammonium chloride solution, the reaction mixture was extracted with ethyl acetate, and the combined organic phases were dried over $Na_2SO_4$ and concentrated in a membrane pump vacuum. After purification by column chromatography (ethyl acetate/cyclohexane), 2-[6-chloro-3-(ethylsulfanyl)pyridin-2-yl]-3,4-dimethyl-6-(trifluoromethyl)-3H-imidazo[4,5-c]pyridine (344 mg, 59%) is obtained as a yellow solid.

HPLC-MS: log P=3.23; Mass (m/z): 387; $^1$H-NMR (d$_6$-DMSO): δ 8.14 (d, 1H), 8.08 (s, 1H), 7.76 (d, 1H), 4.04 (s, 3H), 3.05 (q, 2H), 3.04 (s, 3H), 1.21 (t, 3H).

Synthesis of 2-[6-bromo-3-(ethylsulfanyl)pyridin-2-yl]-4-iodo-3-methyl-6-(trifluoromethyl)-3H-imidazo[4,5-c]pyridine 2-[6-Bromo-3-(ethylsulfanyl)pyridin-2-yl]-3-methyl-6-(trifluoromethyl)-3H-imidazo[4,5-c]pyridine (500 mg, 1.19 mmol) in anhydrous THF (3 ml) was initially charged in a dry, argon-filled 25-ml Schlenk flask, equipped with a magnetic stirrer bar and a septum. Zinc chloride-2,2,6,6-tetramethylpiperidin-1-ide lithium chloride complex (TMPZnCl.LiCl) (1.31M in THF, 1.0 ml, 1.31 mmol) was added dropwise and the mixture was stirred at 80° C. for 30 minutes. The reaction mixture was cooled to 25° C., then iodine (426 mg, 1.67 mmol) was added and the mixture was subsequently stirred at 25° C. for 30 minutes. Saturated aqueous ammonium chloride solution (25 ml) and sodium thiosulfate solution (25 ml) were added to the reaction mixture which was extracted with ethyl acetate (3*50 ml) and dried over anhydrous sodium sulfate. Following filtration, the solvent was removed under reduced pressure. The crude product was purified by chromatography, which gave 2-[6-bromo-3-(ethylsulfanyl)pyridin-2-yl]-4-iodo-3-methyl-6-(trifluoromethyl)-3H-imidazo[4,5-c]pyridine (302 mg, 82%) as a white solid.

HPLC-MS: log P=4.34; Mass (m/z): 543; $^1$H-NMR (d$_6$-DMSO): δ 8.32 (s, 1H), 8.04 (d, 1H), 7.90 (d, 1H), 4.06 (s, 3H), 3.04 (q, 2H), 1.20 (t, 3H).

EXAMPLE 3 (STEP C)

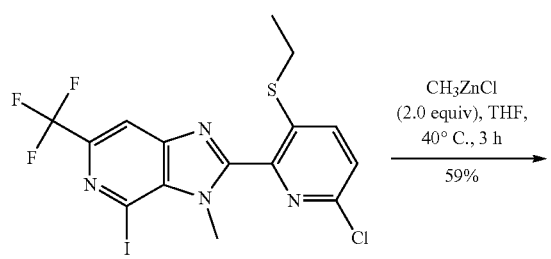

EXAMPLE 4 (STEP C)

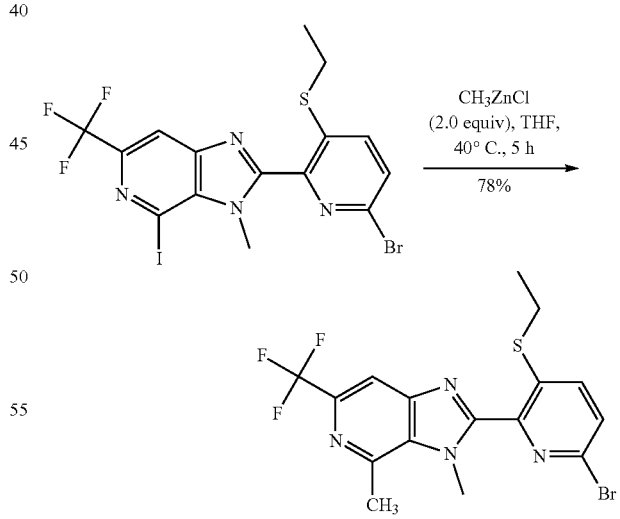

Synthesis of 2-[6-bromo-3-(ethylsulfanyl)pyridin-2-yl]-3,4-dimethyl-6-(trifluoromethyl)-3H-imidazo[4,5-c]pyridine To 2-[6-bromo-3-(ethylsulfanyl)pyridin-2-yl]-4-iodo-3-methyl-6-(trifluoromethyl)-3H-imidazo[4,5-c]pyridine (310 mg, 0.57 mmol), dissolved in THF (3 ml), was added MeZnCl (2.0 M in THF, 0.57 ml, 1.14 mmol) in the presence of tetrakis(triphenylphosphine)palladium(0) (66 mg, 0.05 mmol) at 40° C. under argon; this reaction solution was stirred for 5 hours. After customary workup by addition of saturated ammonium chloride solution, the reaction mixture was extracted with ethyl acetate, and the combined organic phases were dried over Na$_2$SO$_4$ and concentrated in a membrane pump vacuum. After purification by column chromatography (ethyl acetate/cyclohexane), 2-[6-bromo-3-(ethylsulfanyl)pyridin-2-yl]-3,4-dimethyl-6-(trifluoromethyl)-3H-imidazo[4,5-c]pyridine (190 mg, 78%) is obtained as a yellow solid.

HPLC-MS: log P=3.36; Mass (m/z): 431; $^1$H-NMR (d$_6$-DMSO): δ 8.08 (s, 1H), 8.02 (d, 1H), 7.87 (d, 1H), 4.04 (s, 3H), 3.03 (q, 2H), 3.02 (s, 3H), 1.19 (t, 3H).

EXAMPLE 5 (STEP C)

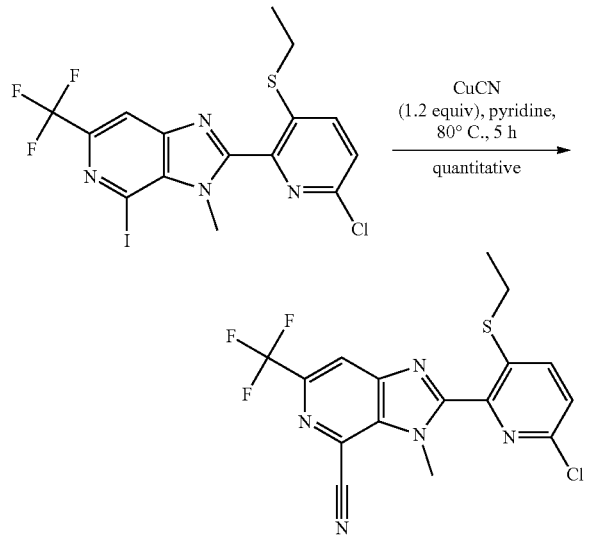

Synthesis of 2-[6-chloro-3-(ethylsulfanyl)pyridin-2-yl]-3-methyl-6-(trifluoromethyl)-3H-imidazo[4,5-c]pyridine-4-carbonitrile To 2-[6-chloro-3-(ethylsulfanyl)pyridin-2-yl]-4-iodo-3-methyl-6-(trifluoromethyl)-3H-imidazo[4,5-c]pyridine (100 mg, 0.20 mmol), dissolved in pyridine (2 ml), was added CuCN (22 mg, 0.24 mmol) at 80° C. under argon; this reaction solution was stirred for 5 hours. After customary workup by addition of saturated sodium chloride and ammonium chloride solutions, the reaction mixture was extracted with ethyl acetate, and the combined organic phases were dried over Na$_2$SO$_4$ and concentrated in a membrane pump vacuum. After purification by column chromatography (ethyl acetate/cyclohexane), 2-[6-chloro-3-(ethylsulfanyl)pyridin-2-yl]-3-methyl-6-(trifluoromethyl)-3H-imidazo[4,5-c]pyridine-4-carbonitrile (99 mg, quantitative) is obtained as a yellow solid.

HPLC-MS: log P=3.84; Mass (m/z): 398; $^1$H-NMR (d$_6$-DMSO): δ 8.73 (s, 11H), 8.18 (d, 11H), 7.79 (d, 11H), 4.14 (s, 3H), 3.05 (q, 2H), 1.21 (t, 3H).

EXAMPLE 6 (STEP C)

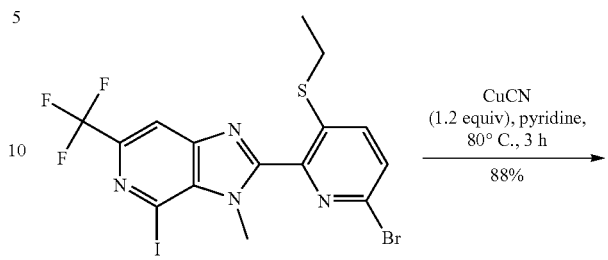

Synthesis of 2-[6-bromo-3-(ethylsulfanyl)pyridin-2-yl]-3-methyl-6-(trifluoromethyl)-3H-imidazo[4,5-c]pyridine-4-carbonitrile To 2-[6-bromo-3-(ethylsulfanyl)pyridin-2-yl]-3-methyl-6-(trifluoromethyl)-3H-imidazo[4,5-c]pyridine (752 mg, 1.03 mmol), dissolved in pyridine (4 ml), was added CuCN (112 mg, 1.24 mmol) at 80° C. under argon; this reaction solution was stirred for 3 hours. After customary workup by addition of saturated sodium chloride and ammonium chloride solutions, the reaction mixture was extracted with ethyl acetate, and the combined organic phases were dried over Na$_2$SO$_4$ and concentrated in a membrane pump vacuum. After purification by column chromatography (ethyl acetate/cyclohexane), 2-[6-bromo-3-(ethylsulfanyl)pyridin-2-yl]-3-methyl-6-(trifluoromethyl)-3H-imidazo[4,5-c]pyridine-4-carbonitrile (473 mg, 88%) is obtained as a yellow solid.

HPLC-MS: log P=3.87; Mass (m/z): 442; $^1$H-NMR (d$_6$-DMSO): δ 8.73 (s, 1H), 8.06 (d, 1H), 7.91 (d, 1H), 4.14 (s, 3H), 3.06 (q, 2H), 1.21 (t, 3H).

EXAMPLE 7 (STEP C)

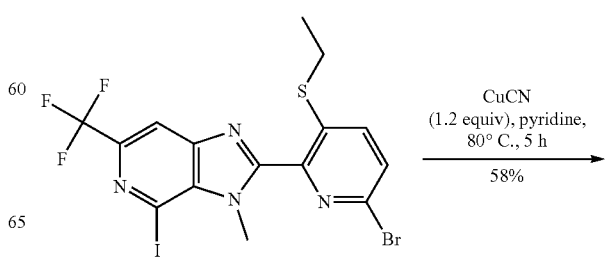

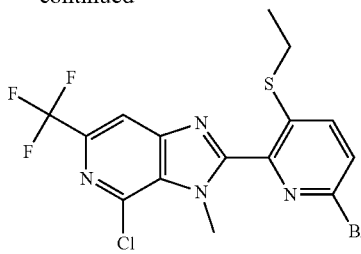

Synthesis of 2-[6-bromo-3-(ethylsulfanyl)pyridin-2-yl]-4-chloro-3-methyl-6-(trifluoromethyl)-3H-imidazo[4,5-c]pyridine To 2-[6-bromo-3-(ethylsulfanyl)pyridin-2-yl]-3-methyl-6-(trifluoromethyl)-3H-imidazo[4,5-c]pyridine (258 mg, 0.47 mmol), dissolved in pyridine (2 ml), was added CuCl (57 mg, 0.57 mmol) at 80° C. under argon; this reaction solution was stirred for 5 hours. After customary workup by addition of saturated sodium chloride and ammonium chloride solutions, the reaction mixture was extracted with ethyl acetate, and the combined organic phases were dried over $Na_2SO_4$ and concentrated in a membrane pump vacuum. After purification by column chromatography (ethyl acetate/cyclohexane), 2-[6-bromo-3-(ethylsulfanyl)pyridin-2-yl]-4-chloro-3-methyl-6-(trifluoromethyl)-3H-imidazo[4,5-c]pyridine (209 mg, 58%) is obtained as a yellow solid.

HPLC-MS: log P=4.18; Mass (m/z): 452; $^1$H-NMR ($d_6$-DMSO): δ 8.39 (s, 1H), 8.07 (d, 1H), 7.90 (d, 1H), 4.07 (s, 3H), 3.04 (q, 2H), 1.20 (t, 3H).

Examples of Further Possible Conversions of Compounds of the Formula (III) to Compounds Effective as Pesticides Oxidation

Synthesis of 2-[6-chloro-3-(ethylsulfonyl)pyridin-2-yl]-3-methyl-6-(trifluoromethyl)-3H-imidazo[4,5-c]pyridine-4-carbonitrile

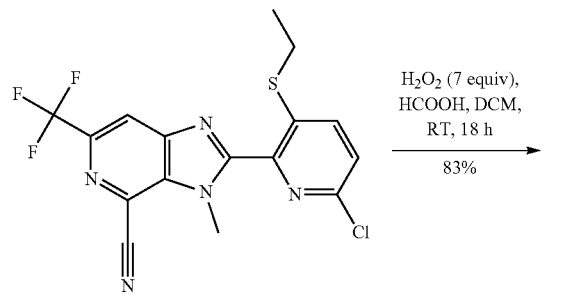

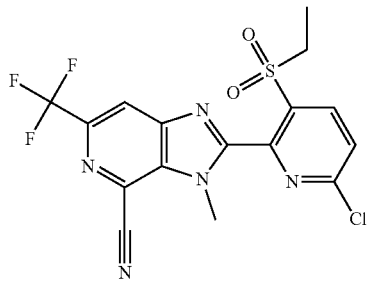

2-[6-Chloro-3-(ethylsulfanyl)pyridin-2-yl]-3-methyl-6-(trifluoromethyl)-3H-imidazo[4,5-c]pyridine-4-carbonitrile (99 mg, 0.24 mmol) in dichloromethane (2 ml) was initially charged in a flask equipped with a magnetic stirrer bar. Formic acid (57 mg, 1.24 mmol) and 35% hydrogen peroxide (169 mg, 1.73 mmol) were then added and the mixture was stirred overnight at 25° C. The reaction mixture was cooled to 25° C. and a dilute HCl solution was then added (to pH 3-4). A little water and a sodium bisulfite solution were added to the reaction mixture followed by a sodium chloride solution and 20% sodium bicarbonate solution, the mixture was extracted with dichloromethane (3*50 ml) and dried over anhydrous sodium sulfate. Following filtration, the solvent was removed under reduced pressure. The crude product was purified by chromatography, which gave 2-[6-chloro-3-(ethylsulfonyl)pyridin-2-yl]-3-methyl-6-(trifluoromethyl)-3H-imidazo[4,5-c]pyridine-4-carbonitrile (94 mg, 83%) as a white solid.

MH$^+$: 430; $^1$H-NMR (400 MHz, $d_6$-DMSO) δ ppm: 1.22 (t, 3H), 3.71 (q, 2H), 4.06 (s, 3H), 8.17 (d, 1H), 8.59 (d, 1H), 8.76 (s, 1H).

Cross-Coupling

Synthesis of 2-[3-(ethylsulfonyl)-6-(1H-1,2,4-triazol-1-yl)pyridin-2-yl]-3-methyl-6-(trifluoromethyl)-3H-imidazo[4,5-c]pyridine-4-carbonitrile (Compound No. 1)

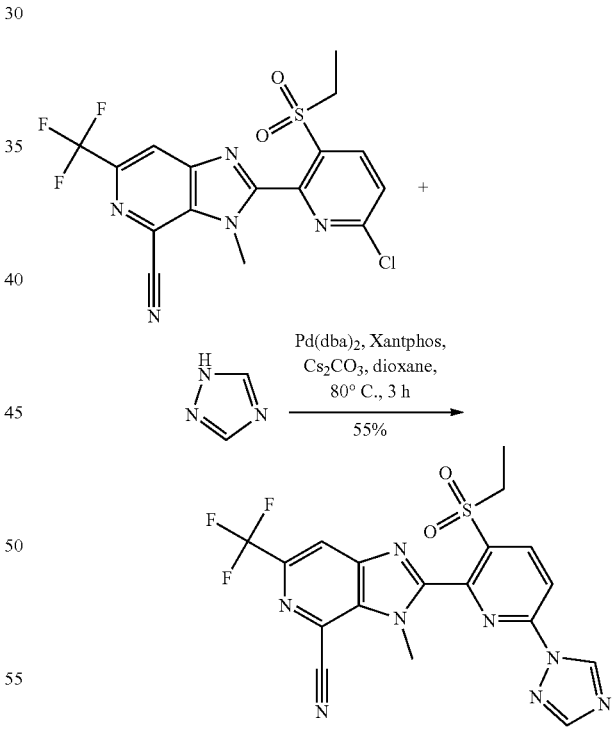

2-[6-Chloro-3-(ethylsulfonyl)pyridin-2-yl]-3-methyl-6-(trifluoromethyl)-3H-imidazo[4,5-c]pyridine-4-carbonitrile (83.6 mg, 0.19 mmol) in anhydrous dioxane (4 ml) was initially charged in a dry, argon-filled 25 ml Schlenk flask, equipped with a magnetic stirrer bar and a septum. 1H-1,2,4-triazole (16.1 mg, 0.23 mmol), caesium carbonate (95.1 mg, 0.29 mmol), 9,9-dimethyl-4,5-bis(diphenylphosphino)xanthene (11.3 mg, 0.02 mmol) and bis(dibenzylideneacetone)palladium(0) (5.6 mg, 0.01 mmol) were then added and the mixture was stirred at 80° C. for 3 h. Saturated aqueous sodium chloride solution (25 ml) was added to the reaction mixture which was extracted with ethyl acetate (3*50 ml) and dried over anhydrous sodium sulfate. Following filtration, the solvent was removed under reduced pressure. The crude product was purified by chromatography, which gave 2-[3-(ethylsulfonyl)-6-(1H-1,2,4-triazol-1-yl)pyridin-2-yl]-3-methyl-6-(trifluoromethyl)-3H-imidazo[4,5-c]pyridine-4-carbonitrile (52.4 mg, 55%) as a white solid.

MH$^+$: 463; $^1$H-NMR (400 MHz, d$_6$-DMSO) δ ppm: 1.23 (t, 3H), 3.84 (q, 2H), 4.19 (s, 3H), 8.37 (d, 1H), 8.475 (s, 1H), 8.79 (d, 1H), 8.80 (s, 1H), 9.52 (s, 1H).

Compounds No. 2 and 3 were prepared analogously to compound No. 1.

| Compound No. | Structure |
|---|---|
| 1 | (structure) |
| 2 | (structure) |
| 3 | (structure) |

USE EXAMPLES

*Myzus persicae*—Oral Test
Solvent: 100 parts by weight of acetone

To produce a suitable active ingredient formulation, 1 part by weight of active ingredient is dissolved with the stated parts by weight of solvent and made up to the desired concentration with water.

50 μl of the active ingredient formulation are transferred into microtitre plates and made up to a final volume of 200 μl with 150 μl of IPL41 insect medium (33%+15% sugar). Subsequently, the plates are sealed with parafilm, which a mixed population of green peach aphids (*Myzus persicae*) within a second microtitre plate is able to puncture and imbibe the solution.

After 5 days, the efficacy in % is determined. 100% means that all the aphids have been killed; 0% means that no aphids have been killed.

In this test, for example, the following compounds from the preparation examples show an efficacy of 100% at an application rate of 4 ppm: 1, 2, 3

*Myzus persicae*—Spray Test

| Solvent: | 78 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 5 days, the efficacy in % is determined. 100% means that all the aphids have been killed; 0% means that no aphids have been killed.

In this test, for example, the following compounds from the preparation examples show an efficacy of 100% at an application rate of 100 g/ha: 3

In this test, for example, the following compounds from the preparation examples show an efficacy of 100% at an application rate of 20 g/ha: 3

In this test, for example, the following compounds from the preparation examples show an efficacy of 90% at an application rate of 20 g/ha: 2

*Phaedon cochleariae*—Spray Test

| Solvent: | 78.0 parts by weight of acetone |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Discs of Chinese cabbage leaves (*Brassica pekinensis*) are sprayed with an active ingredient formularation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples show an efficacy of 83% at an application rate of 100 g/ha: 1, 2

*Spodoptera frugiverda*—Spray Test

| Solvent: | 78.0 parts by weight of acetone |
| --- | --- |
| | 1.5 parts by weight of dimethylformamide |
| Emulsifier: | alkylaryl polyglycol ether |

To produce a suitable active ingredient formulation, 1 part by weight of active ingredient is dissolved with the specified parts by weight of solvent and made up to the desired concentration with water containing an emulsifier concentration of 1000 ppm. To produce further test concentrations, the formulation is diluted with emulsifier-containing water.

Leaf discs of maize (*Zea mays*) are sprayed with an active ingredient formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples show an efficacy of 100% at an application rate of 100 g/ha: 3

The invention claimed is:
1. Method for preparing a compound of formula (II)

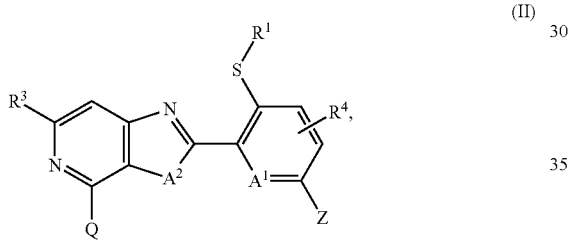

(II)

in which
Q and Z are each independently halogen,
$A^1$ is nitrogen, =$N^+O^-$ or =C—$R^5$,
$A^2$ is —N—$R^6$, oxygen or sulfur,
$R^1$ is ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_6$)alkyl, ($C_2$-$C_6$)haloalkynyloxy-($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_6$)halocycloalkyl, ($C_3$-$C_6$)cyanocycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, amino, ($C_1$-$C_6$)alkylamino, di($C_1$-$C_6$)alkylamino, ($C_3$-$C_8$)cycloalkylamino, ($C_1$-$C_6$)alkylcarbonylamino, ($C_1$-$C_6$)alkylthio-($C_1$-$C_6$)alkyl, ($C_1$-$C_6$)haloalkylthio-($C_1$-$C_6$)alkyl, ($C_1$-$C_6$)alkylsulfinyl-($C_1$-$C_6$)alkyl, ($C_1$-$C_6$)haloalkylsulfinyl-($C_1$-$C_6$)alkyl, ($C_1$-$C_6$)alkylsulfonyl-($C_1$-$C_6$)alkyl, ($C_1$-$C_6$)haloalkylsulfonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulfinyl-($C_1$-$C_6$)alkyl, ($C_1$-$C_6$)alkoxy-($C_1$-$C_6$)alkylsulfonyl-($C_1$-$C_6$)alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxycarbonyl-($C_1$-$C_6$)alkyl, ($C_1$-$C_6$)haloalkoxycarbonyl-($C_1$-$C_6$)alkyl, ($C_1$-$C_6$)alkylsulfonylamino, aminosulfonyl-($C_1$-$C_6$)alkyl, ($C_1$-$C_6$)alkylaminosulfonyl-($C_1$-$C_6$)alkyl, di($C_1$-$C_6$)alkylaminosulfonyl-($C_1$-$C_6$)alkyl,
or is ($C_1$-$C_6$)alkyl, ($C_1$-$C_6$)alkoxy, ($C_2$-$C_6$)alkenyl, ($C_2$-$C_6$)alkynyl, ($C_3$-$C_8$)cycloalkyl, each of which is optionally mono- or polysubstituted by identical or different substituents from the group consisting of aryl, hetaryl and heterocyclyl, where aryl, hetaryl or heterocyclyl may each optionally be mono- or polysubstituted by identical or different substituents from the group consisting of halogen, cyano, nitro, hydroxyl, amino, carboxy, carbamoyl, aminosulfonyl, ($C_1$-$C_6$)alkyl, ($C_3$-$C_6$)cycloalkyl, ($C_1$-$C_6$)alkoxy, ($C_1$-$C_6$)haloalkyl, ($C_1$-$C_6$)haloalkoxy, ($C_1$-$C_6$)alkylthio, ($C_1$-$C_6$)alkylsulfinyl, ($C_1$-$C_6$)alkylsulfonyl, ($C_1$-$C_6$)alkylsulfimino, ($C_1$-$C_6$)alkylsulfimino-($C_1$-$C_6$)alkyl, ($C_1$-$C_6$)alkylsulfimino-($C_2$-$C_6$)alkylcarbonyl, ($C_1$-$C_6$)alkylsulfoximino, ($C_1$-$C_6$)alkylsulfoximino-($C_1$-$C_6$)alkyl, ($C_1$-$C_6$)alkylsulfoximino-($C_2$-$C_6$)alkylcarbonyl, ($C_1$-$C_6$)alkoxycarbonyl, ($C_1$-$C_6$)alkylcarbonyl, ($C_3$-$C_6$)trialkylsilyl and benzyl
$R^3$ is hydrogen, cyano, halogen, nitro, acetyl, hydroxyl, amino, SCN, tri($C_1$-$C_6$)alkylsiyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, cyano($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di($C_1$-$C_6$)alkylaminocarbonyl, di($C_1$-$C_6$)alkylaminothiocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, —NHCO-($C_1$-$C_6$)alkyl ((($C_1$-$C_6$)alkylcarbonylamino), or
is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, tri($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)-alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl or ($C_3$-$C_8$)cycloalkylamino, $R^4$ is hydrogen, cyano, halogen, nitro, acetyl, hydroxyl, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, cyano($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di($C_1$-$C_6$)alkylaminocarbonyl, di($C_1$-$C_6$)alkylaminothiocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, NHCO—($C_1$-$C_6$)alkyl, ($C_1$-$C_6$)alkylcarbonylamino), or is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, ($C_1$-$C_6$)alkylcarbonylamino, $R^5$ is hydrogen, cyano, halogen, nitro, acetyl, hydroxyl, amino, SCN, tri($C_1$-$C_6$)alkylsilyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkylhydroxyimino, ($C_1$-$C_6$)alkoxyimino, ($C_1$-$C_6$)alkyl-($C_1$-$C_6$)alkoxyimino, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)alkylthiocarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, ($C_1$-$C_6$)alkylaminothiocarbonyl, di($C_1$-$C_6$)alkylaminocarbonyl, di($C_1$-$C_6$)alkylaminothiocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino or —NHCO—($C_1$-$C_6$)alkyl (($C_1$-$C_6$)alkylcarbonylamino) and $R^6$ is ($C_1$-$C_6$)alkyl, ($C_1$-$C_6$)haloalkyl, ($C_1$-$C_6$)cyanoalkyl, ($C_1$-$C_6$)hydroxyalkyl, ($C_1$-$C_6$)alkoxy-($C_1$-$C_6$)alkyl, ($C_1$-$C_6$)haloalkoxy-($C_1$-$C_6$)alkyl, ($C_2$-$C_6$)alkenyl, ($C_2$-$C_6$)alkenyloxy-($C_1$-$C_6$)alkyl, ($C_2$-$C_6$)haloalkenyloxy-($C_1$-$C_6$)alkyl, ($C_2$-$C_6$)haloalkenyl, ($C_2$-$C_6$)cyanoalkenyl, ($C_2$-$C_6$)alkynyl, ($C_2$-$C_6$)alkynyloxy-($C_1$-$C_6$)alkyl, ($C_2$-$C_6$)haloalkynyloxy-($C_1$-$C_6$)alkyl, ($C_2$-$C_6$)haloalkynyl, ($C_2$-$C_6$)cyanoalkynyl, ($C_3$-$C_8$)cycloalkyl, ($C_3$-$C_8$)cycloalkyl-($C_3$-$C_8$)cycloalkyl, ($C_1$-$C_6$)alkyl-($C_3$-$C_8$)cycloalkyl, halo($C_3$-$C_8$)cycloalkyl, ($C_1$-$C_6$)alkylthio-($C_1$-$C_6$)alkyl, ($C_1$-$C_6$)haloalkylthio-($C_1$-$C_6$)alkyl, ($C_1$-$C_6$)alkylsulfinyl-($C_1$-$C_6$)alkyl, ($C_1$-$C_6$)haloalkylsulfinyl-($C_1$-$C_6$)alkyl, ($C_1$-$C_6$)alkylsulfonyl-($C_1$-$C_6$)alkyl, ($C_1$-$C_6$)haloalkylsulfonyl-($C_1$-$C_6$)alkyl, ($C_1$-$C_6$)alkoxy-($C_1$-$C_6$)alkylthio-($C_1$-$C_6$)alkyl, ($C_1$-$C_6$)alkoxy-($C_1$-$C_6$)alkylsulfinyl-($C_1$-$C_6$)alkyl, ($C_1$-$C_6$)alkoxy-($C_1$-$C_6$)alkylsulfonyl-($C_1$-$C_6$)alkyl, ($C_1$-$C_6$)alkylcarbonyl-($C_1$-$C_6$)alkyl, ($C_1$-$C_6$)haloalkylcarbonyl-($C_1$-$C_6$)alkyl, ($C_1$-$C_6$)alkoxycarbonyl-($C_1$-$C_6$)alkyl, ($C_1$-$C_6$)haloalkoxycarbonyl-($C_1$-$C_6$)alkyl, aminocarbonyl-($C_1$-$C_6$)alkyl, ($C_1$-$C_6$)alkylamino-($C_1$-$C_6$)alkyl, di($C_1$-$C_6$)alkylamino-($C_1$-$C_6$)alkyl or ($C_3$-$C_8$)cycloalkylamino-($C_1$-$C_6$)alkyl, comprising reacting, a), a compound of formula (I)

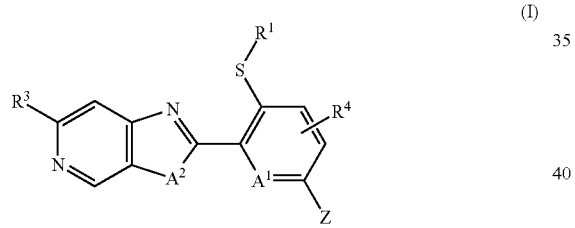

(I)

in which Z, $R^1$, $R^3$, $R^4$, $A^1$ and $A^2$ are each as defined above, with an organozinc base of the structure (NR$^a$R$^b$)—Zn—R$^c$ or (NR$^a$R$^b$)$_2$—Zn, in which R$^c$ is halogen or —O-pivaloyl and R$^a$ and R$^b$ together form a —(CH$_2$)$_4$—, —(CH$_2$)$_5$— or —(CH$_2$)$_2$O(CH$_2$)$_2$— group, where each of these groups may optionally be substituted by 1, 2, 3 or 4 R$^d$ radicals and R$^d$ is selected from the group consisting of methyl, ethyl, n-propyl and isopropyl, to give a compound of formula (IVa) or formula (IVb),

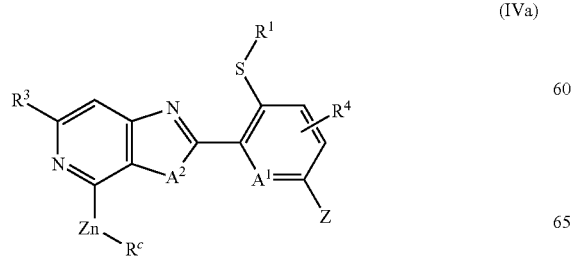

(IVa)

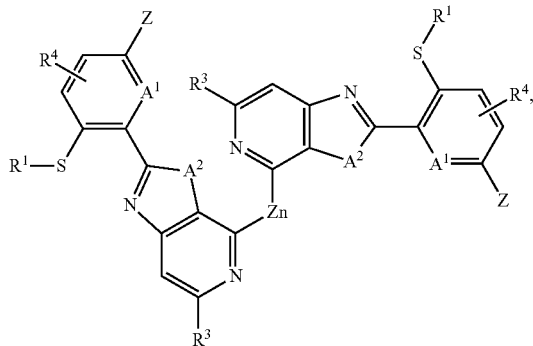

(IVb)

in which Z, $R^1$, $R^3$, $R^4$, $R^c$, $A^1$ and $A^2$ are each as defined above, and this compound of formula (IVa) or (IVb) is reacted in b) with a compound of the structure Q-V, in which V is halogen and Q has the abovementioned definition, to give the compound of formula (II).

2. Method according to claim 1, wherein

Q is chlorine, iodine or bromine,

Z is bromine, fluorine or chlorine,

R$^c$ is —O-pivaloyl, chlorine, bromine or iodine, $A^1$ is nitrogen, =N$^+$—O$^-$ or =C—R$^5$, $A^2$ is —N—R$^6$ or oxygen, $R^1$ is ($C_1$-$C_4$)alkyl, ($C_1$-$C_4$)hydroxyalkyl, ($C_1$-$C_4$)haloalkyl, ($C_1$-$C_4$)cyanoalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyloxy-($C_1$-$C_4$)alkyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylamino, di($C_1$-$C_4$)alkylamino, ($C_3$-$C_6$)cycloalkylamino, ($C_1$-$C_4$)alkylcarbonylamino, ($C_1$-$C_4$)alkylthio-($C_1$-$C_4$)alkyl, ($C_1$-$C_4$)haloalkylthio-($C_1$-$C_4$)alkyl, ($C_1$-$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)alkylcarbonyl-($C_1$-$C_4$)alkyl, ($C_1$-$C_4$)haloalkylcarbonyl-($C_1$-$C_4$)alkyl, ($C_1$-$C_4$)alkylsulfonylamino, or is ($C_1$-$C_4$)alkyl, ($C_1$-$C_4$)alkoxy, ($C_2$-$C_4$)alkenyl, ($C_2$-$C_4$)alkynyl or ($C_3$-$C_6$)cycloalkyl, each of which is optionally mono- or disubstituted by identical or different substituents from the group consisting of aryl, hetaryl and heterocyclyl, where aryl, hetaryl or heterocyclyl may each optionally be mono- or disubstituted by identical or different substituents from the group consisting of halogen, cyano, carbamoyl, aminosulfonyl, ($C_1$-$C_4$)alkyl, ($C_3$-$C_4$)cycloalkyl, ($C_1$-$C_4$)alkoxy, ($C_1$-$C_4$)haloalkyl, ($C_1$-$C_4$)haloalkoxy, ($C_1$-$C_4$)alkylthio, ($C_1$-$C_4$)alkylsulfinyl, ($C_1$-$C_4$)alkylsulfonyl and ($C_1$-$C_4$)alkylsulfimino, $R^3$ is hydrogen, cyano, halogen, nitro, acetyl, hydroxyl, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano($C_3$-$C_8$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-

$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, aminothiocarbonyl, NHCO—($C_1$-$C_4$)alkyl (($C_1$-$C_4$)alkylcarbonylamino) or is phenyl or hetaryl, each of which is optionally mono- or disubstituted by identical or different substituents, where (in the case of hetaryl) at least one carbonyl group may optionally be present and where possible substituents in each case are as follows: cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl and di($C_1$-$C_4$)alkylaminosulfonyl, $R^4$ is hydrogen, cyano, halogen, nitro, acetyl, hydroxyl, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, cyano($C_3$-$C_8$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, aminothiocarbonyl, NHCO—($C_1$-$C_4$)alkyl (($C_1$-$C_4$)alkylcarbonylamino), is furthermore phenyl or hetaryl, each of which is optionally mono- or disubstituted by identical or different substituents, where (in the case of hetaryl) at least one carbonyl group may optionally be present and where possible substituents in each case are as follows: cyano, halogen, nitro, acetyl, amino, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, NHCO—($C_1$-$C_4$)alkyl(($C_1$-$C_4$)alkylcarbonylamino), $R^5$ is hydrogen, cyano, halogen, nitro, acetyl, hydroxyl, amino, SCN, tri($C_1$-$C_4$)alkylsilyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, aminothiocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, aminothiocarbonyl or NHCO—($C_1$-$C_4$)alkyl (($C_1$-$C_4$)alkylcarbonylamino) and $R^6$ is ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_1$-$C_4$)haloalkoxy-($C_1$-$C_4$)alkyl, ($C_2$-$C_4$)alkenyl, ($C_2$-$C_4$)alkenyloxy-($C_1$-$C_4$)alkyl, ($C_2$-$C_4$)haloalkenyloxy-($C_1$-$C_4$)alkyl, ($C_2$-$C_4$)haloalkenyl, ($C_2$-$C_4$)cyanoalkenyl, ($C_2$-$C_4$)alkynyl, ($C_2$-$C_4$)alkynyloxy-($C_1$-$C_4$)alkyl, ($C_2$-$C_4$)haloalkynyl, ($C_3$-$C_6$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkylthio-($C_1$-$C_4$)alkyl, ($C_1$-$C_4$)haloalkylthio-($C_1$-$C_4$)alkyl, ($C_1$-

$C_4$)alkylsulfinyl-($C_1$-$C_4$)alkyl, ($C_1$-$C_4$)haloalkylsulfinyl-($C_1$-$C_4$)alkyl, ($C_1$-$C_4$)alkylsulfonyl-($C_1$-$C_4$)alkyl, ($C_1$-$C_4$)haloalkylsulfonyl-($C_1$-$C_4$)alkyl, ($C_1$-$C_4$)alkoxy-($C_1$-$C_4$)alkylthio-($C_1$-$C_4$)alkyl or ($C_1$-$C_4$)alkylcarbonyl-($C_1$-$C_4$)-alkyl.

3. Method according to claim 1, wherein
Q is chlorine, iodine or bromine,
Z is bromine, fluorine or chlorine,
$R^c$ is —O-pivaloyl, chlorine, bromine or iodine,
$A^1$ is nitrogen or =C—$R^5$,
$A^2$ is —N—$R^6$,
$R^1$ is ($C_1$-$C_4$)alkyl, ($C_1$-$C_4$)hydroxyalkyl, ($C_1$-$C_4$)haloalkyl, ($C_2$-$C_4$)alkenyl, ($C_2$-$C_4$)haloalkenyl, ($C_2$-$C_4$)alkynyl, ($C_2$-$C_4$)haloalkynyl, ($C_3$-$C_6$)cycloalkyl, ($C_1$-$C_4$)alkylthio-($C_1$-$C_4$)alkyl, ($C_1$-$C_4$)alkylsulfinyl-($C_1$-$C_4$)alkyl or ($C_1$-$C_4$)alkylsulfonyl-($C_1$-$C_4$)alkyl,
$R^3$ is hydrogen, halogen, ($C_1$-$C_4$)alkyl, ($C_1$-$C_4$)haloalkyl, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)haloalkylthio, ($C_1$-$C_4$)haloalkylsulfinyl or ($C_1$-$C_4$)haloalkylsulfonyl,
$R^4$ is hydrogen, cyano, halogen, nitro, hydroxyl, amino, SCN, tri($C_1$-$C_4$)alkylsilyl, ($C_3$-$C_6$)cycloalkyl, cyano($C_3$-$C_8$)cycloalkyl, ($C_3$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)cyanoalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl or NHCO—($C_1$-$C_4$)alkyl (($C_1$-$C_4$)alkylcarbonylamino),
is furthermore phenyl or hetaryl, each of which is optionally mono- or disubstituted by identical or different substituents, where (in the case of hetaryl) at least one carbonyl group may optionally be present and where possible substituents in each case are as follows: cyano, halogen, ($C_3$-$C_6$)cycloalkyl, ($C_1$-$C_6$)cycloalkyl-($C_3$-$C_6$)cycloalkyl, ($C_1$-$C_4$)alkyl-($C_3$-$C_6$)cycloalkyl, halo($C_3$-$C_6$)cycloalkyl, ($C_1$-$C_4$)alkyl, ($C_1$-$C_4$)haloalkyl, ($C_1$-$C_4$)cyanoalkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_1$-$C_4$)alkoxy, ($C_1$-$C_4$)haloalkoxy, ($C_1$-$C_4$)alkylhydroxyimino, ($C_1$-$C_4$)alkoxyimino, ($C_1$-$C_4$)alkyl-($C_1$-$C_4$)alkoxyimino, ($C_1$-$C_4$)alkylthio, ($C_1$-$C_4$)haloalkylthio, ($C_1$-$C_4$)alkylsulfinyl, ($C_1$-$C_4$)haloalkylsulfinyl, ($C_1$-$C_4$)alkylsulfonyl, ($C_1$-$C_4$)haloalkylsulfonyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, NHCO—($C_1$-$C_4$)alkyl (($C_1$-$C_4$)alkylcarbonylamino),
$R^5$ is hydrogen, halogen, cyano or ($C_1$-$C_4$)alkyl and
$R^6$ is ($C_1$-$C_4$)alkyl or ($C_1$-$C_4$)alkoxy-($C_1$-$C_4$)alkyl.

4. Method according to claim 1, wherein
Q is iodine or bromine,
Z is bromine or chlorine,
$R^c$ is chlorine, bromine or iodine,
$A^1$ is nitrogen or =C—$R^5$,
$A^2$ is —N—$R^6$,
$R^1$ is methyl, ethyl, n-propyl, isopropyl, cyclopropyl, n-butyl, isobutyl, tert-butyl, cyclobutyl, fluoromethyl, difluoromethyl, trifluoromethyl, fluoroethyl, difluoroethyl, trifluoroethyl, tetrafluoroethyl or pentafluoroethyl,
$R^3$ is fluorine, chlorine, fluoromethyl, difluoromethyl, trifluoromethyl, fluoroethyl, difluoroethyl, trifluoroethyl, tetrafluoroethyl, pentafluoroethyl, trifluoromethoxy, difluorochloromethoxy, dichlorofluoromethoxy, trifluoromethylthio, trifluoromethylsulfonyl or trifluoromethylsulfinyl,
$R^4$ is hydrogen, cyano, halogen, ($C_1$-$C_4$)alkyl, ($C_1$-$C_4$)haloalkyl, ($C_1$-$C_4$)haloalkoxy, ($C_1$-$C_4$)alkylthio, ($C_1$-$C_4$)alkylsulfinyl, ($C_1$-$C_4$)alkylsulfonyl, ($C_1$-$C_4$)haloalkylthio, ($C_1$-$C_4$)haloalkylsulfinyl, ($C_1$-$C_4$)haloalkylsulfonyl or NHCO—($C_1$-$C_4$)alkyl (($C_1$-$C_4$)alkylcarbonylamino),
$R^5$ is hydrogen, fluorine, chlorine, bromine or cyano and
$R^6$ is methyl, ethyl, isopropyl, methoxymethyl or methoxyethyl.

5. Method according to claim 1, wherein
Q is iodine or bromine,
Z is bromine or chlorine,
$R^c$ is chlorine or bromine,
$A^1$ is nitrogen,
$A^2$ is —N—$R^6$,
$R^1$ is methyl, ethyl, n-propyl, isopropyl or cyclopropyl,
$R^3$ is trifluoromethyl or pentafluoroethyl,
$R^4$ is hydrogen and
$R^6$ is methyl.

6. Method according to claim 1, wherein
Q is iodine or bromine,
Z is bromine or chlorine,
$R^c$ is chlorine,
$A^1$ is nitrogen,
$A^2$ is —N—$R^6$,
$R^1$ is ethyl,
$R^3$ is trifluoromethyl,
$R^4$ is hydrogen and
$R^6$ is methyl.

7. Method according to claim 1, wherein the organozinc base is a compound of formula (VI)

$$(TMP)_x ZnCl_{2-x},\quad (VI)$$

in which x is the number 1 or 2.

8. Method according to claim 1, wherein the organozinc base is present in conjunction with an alkali metal halide or alkaline earth metal halide, optionally lithium chloride and/or magnesium chloride.

9. Method according to claim 1, wherein the compound Q-V is an elemental halogen, optionally $F_2$, $Cl_2$, $Br_2$ or $I_2$.

10. Method according to claim 1, wherein the solvent is THF or N,N-dimethylformamide (DMF).

11. Method according to claim 1, wherein a) is conducted at a temperature between 0° C. and 80° C.

12. Method according to claim 1, wherein b) is conducted at a temperature between 0° C. and 80° C.

13. Method according to claim 1, wherein the compound of formula (II) is further reacted in c) to give a compound of formula (III)

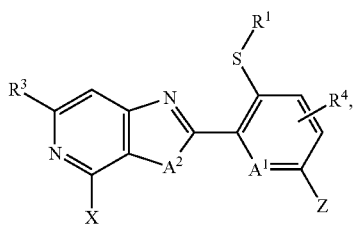

(III)

in which

X is cyano, carboxyl, halogen, nitro, acetyl, hydroxyl, amino, SCN, tri($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_1$-$C_6$)cycloalkyl ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkoxyimino, —N=C(H)—O($C_1$-$C_6$)alkyl, —C(H)=N—O($C_1$-$C_6$)alkyl, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino, ($C_1$-$C_6$)alkylcarbamoyl (including —NHCOO($C_1$-$C_6$)alkyl, —N($C_1$-$C_6$)alkylCOO($C_1$-$C_6$)alkyl, —OCONH($C_1$-$C_6$)alkyl or —OCON($C_1$-$C_6$)dialkyl), ($C_1$-$C_6$)alkylcarbonylamino (($C_1$-$C_6$)alkylCONH), ($C_1$-$C_6$)alkylurea (including —NHCONH($C_1$-$C_6$)alkyl, and —NHCON($C_1$-$C_6$)dialkyl) or is a saturated, partially saturated or heteroaromatic ring which is optionally mono- or polysubstituted by identical or different substituents and in which at least one carbon atom is replaced by a heteroatom, or is an aromatic ring which is mono- or polysubstituted by identical or different substituents, where at least one carbonyl group may optionally be present in each case and where possible substituents in each case are as follows: cyano, carboxyl, halogen, nitro, acetyl, hydroxyl, amino, SCN, tri($C_1$-$C_6$)alkylsilyl, ($C_1$-$C_6$)alkyl, ($C_1$-$C_6$)haloalkyl, ($C_1$-$C_6$)cyanoalkyl, ($C_1$-$C_6$)hydroxyalkyl, hydroxycarbonyl-($C_1$-$C_6$)-alkoxy, ($C_1$-$C_6$)alkoxycarbonyl-($C_1$-$C_6$)alkyl, ($C_1$-$C_6$)alkoxy-($C_1$-$C_6$)alkyl, ($C_2$-$C_6$)alkenyl, ($C_2$-$C_6$)haloalkenyl, ($C_2$-$C_6$)cyanoalkenyl, ($C_2$-$C_6$)alkynyl, ($C_2$-$C_6$)haloalkynyl, ($C_2$-$C_6$)cyanoalkynyl, ($C_3$-$C_6$)cycloalkyl, ($C_3$-$C_6$)halocycloalkyl, ($C_3$-$C_6$)cyanocycloalkyl, ($C_1$-$C_6$)cycloalkyl-($C_3$-$C_6$)cycloalkyl, ($C_1$-$C_4$)alkyl-($C_1$-$C_6$)cycloalkyl ($C_1$-$C_6$)alkoxy, ($C_1$-$C_6$)haloalkoxy, ($C_1$-$C_6$)cyanoalkoxy, ($C_1$-$C_6$)alkoxycarbonyl-($C_1$-$C_6$)alkoxy, ($C_1$-$C_6$)alkoxy-($C_1$-$C_6$)alkoxy, ($C_1$-$C_6$)alkoxyimino, —N=C(H)—O($C_1$-$C_6$)alkyl, —C(H)=N—O($C_1$-$C_6$)alkyl, ($C_1$-$C_6$)haloalkyl-($C_1$-$C_6$)alkoxyimino, ($C_1$-$C_6$)alkylthio, ($C_1$-$C_6$)haloalkylthio, ($C_1$-$C_6$)alkoxy-($C_1$-$C_6$)alkylthio, ($C_1$-$C_6$)alkylthio-($C_1$-$C_6$)alkyl, ($C_1$-$C_6$)alkylsulfinyl, ($C_1$-$C_6$)haloalkylsulfinyl, ($C_1$-$C_6$)alkoxy-($C_1$-$C_6$)alkylsulfinyl, ($C_1$-$C_6$)alkylsulfinyl-($C_1$-$C_6$)alkyl, ($C_1$-$C_6$)alkylsulfonyl, ($C_1$-$C_6$)haloalkylsulfonyl, ($C_1$-$C_6$)alkoxy-($C_1$-$C_6$)alkylsulfonyl, ($C_1$-$C_6$)alkylsulfonyl-($C_1$-$C_6$)alkyl, ($C_1$-$C_6$)alkylsulfonyloxy, ($C_1$-$C_6$)alkylcarbonyl, ($C_1$-$C_6$)haloalkylcarbonyl, ($C_1$-$C_6$)alkylcarbonyloxy, ($C_1$-$C_6$)alkoxycarbonyl, ($C_1$-$C_6$)haloalkoxycarbonyl, aminocarbonyl, ($C_1$-$C_6$)alkylaminocarbonyl, di($C_1$-$C_6$)alkylaminocarbonyl, ($C_2$-$C_6$)alkenylaminocarbonyl, di($C_2$-$C_6$)alkenylaminocarbonyl, ($C_3$-$C_8$)cycloalkylaminocarbonyl, ($C_1$-$C_6$)alkylsulfonylamino, ($C_1$-$C_6$)alkylamino, di($C_1$-$C_6$)alkylamino, aminosulfonyl, ($C_1$-$C_6$)alkylaminosulfonyl, di($C_1$-$C_6$)alkylaminosulfonyl, ($C_1$-$C_6$)alkylsulfoximino, aminothiocarbonyl, ($C_1$-$C_6$)alkylaminothiocarbonyl, di($C_1$-$C_6$)alkylaminothiocarbonyl, ($C_3$-$C_8$)cycloalkylamino or ($C_1$-$C_6$)alkylcarbonylamino.

14. Method according to claim 13, wherein

X is cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)cyanoalkoxy, ($C_1$-$C_4$)alkoxy-($C_1$-$C_4$)alkoxy, ($C_1$-$C_4$)alkoxyimino, —N=C(H)—O($C_1$-$C_4$)alkyl, —C(H)=N—O($C_1$-$C_4$)alkyl, ($C_1$-$C_4$)haloalkyl-($C_1$-$C_4$)alkoxyimino, ($C_1$-$C_4$)alkylthio, ($C_1$-$C_4$)haloalkylthio, ($C_1$-$C_4$)alkylthio-($C_1$-$C_4$)alkyl, ($C_1$-$C_4$)alkylsulfinyl, ($C_1$-$C_4$)haloalkylsulfinyl, ($C_1$-$C_4$)alkylsulfinyl-($C_1$-$C_4$)alkyl, ($C_1$-$C_4$)alkylsulfonyl, ($C_1$-$C_4$)haloalkylsulfonyl, ($C_1$-$C_4$)alkylsulfonyl-($C_1$-$C_4$)alkyl, ($C_1$-$C_4$)alkylsulfonyloxy, ($C_1$-$C_4$)alkylcarbonyl, ($C_1$-$C_4$)haloalkylcarbonyl, aminocarbonyl, ($C_1$-$C_4$)alkylaminocarbonyl, di($C_1$-$C_4$)alkylaminocarbonyl, ($C_1$-$C_4$)alkylsulfonylamino, ($C_1$-$C_4$)alkylamino, di($C_1$-$C_4$)alkylamino, aminosulfonyl, ($C_1$-$C_4$)alkylaminosulfonyl, di($C_1$-$C_4$)alkylaminosulfonyl, ($C_1$-$C_4$)alkylcarbamoyl (including —NHCOO($C_1$-$C_4$)alkyl, —N($C_1$-$C_4$)alkylCOO($C_1$-$C_4$)alkyl, —OCONH($C_1$-$C_4$)alkyl or —OCON($C_1$-$C_4$)dialkyl), ($C_1$-$C_4$)alkylcarbonylamino (($C_1$-$C_4$)alkylCONH) or ($C_1$-$C_4$)alkylurea (including —NHCONH($C_1$-$C_6$)alkyl and —NHCON($C_1$-$C_6$)dialkyl).

15. Method according to claim 13, wherein

X is cyano, halogen, nitro, acetyl, amino, ($C_1$-$C_4$)alkyl, ($C_1$-$C_4$)haloalkyl, ($C_1$-$C_4$)cyanoalkyl, ($C_1$-$C_4$)hydroxyalkyl, ($C_1$-$C_4$)alkoxy-($C_1$-$C_4$)alkyl, ($C_2$-$C_4$)alkenyl, ($C_2$-$C_4$)haloalkenyl, ($C_2$-$C_4$)cyanoalkenyl, ($C_2$-$C_4$)alkynyl, ($C_2$-$C_4$)haloalkynyl, ($C_2$-$C_4$)cyanoalkynyl, ($C_3$-$C_6$)cycloalkyl, ($C_3$-$C_6$)halocycloalkyl, ($C_3$-$C_6$)cyanocycloalkyl, ($C_3$-$C_6$)cycloalkyl-($C_3$-$C_6$)cycloalkyl, ($C_1$-$C_4$)alkyl-($C_3$-$C_6$)cycloalkyl, ($C_1$-$C_4$)alkoxy, ($C_1$-$C_4$)haloalkoxy, ($C_1$-$C_4$)cyanoalkoxy or ($C_1$-$C_4$)alkoxy-($C_1$-$C_4$)alkoxy.

16. Method according to claim 13, wherein
X is cyano, halogen, amino, $(C_1-C_4)$alkyl, $(C_1-C_4)$haloalkyl, $(C_1-C_4)$cyanoalkyl, $(C_1-C_4)$hydroxyalkyl, $(C_1-C_4)$alkoxy-$(C_1-C_4)$alkyl, $(C_2-C_4)$alkenyl, $(C_2-C_4)$haloalkenyl, $(C_2-C_4)$cyanoalkenyl, $(C_2-C_4)$alkynyl, $(C_2-C_4)$haloalkynyl, $(C_2-C_4)$cyanoalkynyl, $(C_3-C_6)$cycloalkyl, $(C_3-C_6)$halocycloalkyl, $(C_3-C_6)$cyanocycloalkyl, $(C_3-C_6)$cycloalkyl-$(C_3-C_6)$cycloalkyl, $((C_1-C_4)$alkoxy or $(C_1-C_4)$cyanoalkoxy.

17. Method according to claim 13, wherein the reaction in c) is conducted at a temperature between 0° C. and 110° C.

18. Method according to claim 13, wherein the compound of formula (II) is reacted with one or more organozinc reagents in the presence of a catalyst or with one or more metal salts.

19. Compound of formula (II)

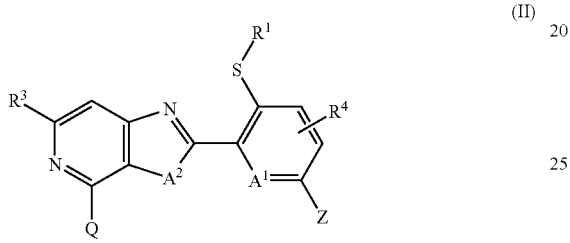

(II)

in which

Q and Z are each independently halogen, $A^1$ is nitrogen, $=N^+O^-$ or $=C-R^5$, $A^2$ is $-N-R^6$, oxygen or sulfur, $R^1$ is $(C_1-C_6)$alkyl, $(C_1-C_6)$haloalkyl, $(C_1-C_6)$cyanoalkyl, $(C_1-C_6)$hydroxyalkyl, $(C_1-C_6)$alkoxy-$(C_1-C_6)$alkyl, $(C_1-C_6)$haloalkoxy-$(C_1-C_6)$alkyl, $(C_2-C_6)$alkenyl, $(C_2-C_6)$alkenyloxy-$(C_1-C_6)$alkyl, $(C_2-C_6)$haloalkenyloxy-$(C_1-C_6)$alkyl, $(C_2-C_6)$haloalkenyl, $(C_2-C_6)$cyanoalkenyl, $(C_2-C_6)$alkynyl, $(C_2-C_6)$alkynyloxy-$(C_1-C_6)$alkyl, $(C_2-C_6)$haloalkynyloxy-$(C_1-C_6)$alkyl, $(C_2-C_6)$haloalkynyl, $(C_2-C_6)$cyanoalkynyl, $(C_3-C_8)$cycloakyl, $(C_3-C_6)$halocycloalkyl, $(C_3-C_6)$cyanocycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, amino, $(C_1-C_6)$alkylamino, di$(C_1-C_6)$alkylamino, $(C_3-C_8)$cycloalkylamino, $(C_1-C_6)$alkylcarbonylamino, $(C_1-C_6)$alkylthio-$(C_1-C_6)$alkyl, $(C_1-C_6)$haloalkylthio-$(C_1-C_6)$alkyl, $(C_1-C_6)$alkylsulfinyl-$(C_1-C_6)$alkyl, $(C_1-C_6)$haloalkylsulfinyl-$(C_1-C_6)$alkyl, $(C_1-C_6)$alkylsulfonyl-$(C_1-C_6)$alkyl, $(C_1-C_6)$haloalkylsulfonyl-$(C_1-C_6)$alkyl, $(C_1-C_6)$alkoxy-$(C_1-C_6)$alkylthio-$(C_1-C_6)$alkyl, $(C_1-C_6)$alkoxy-$(C_1-C_6)$alkylsulfinyl-$(C_1-C_6)$alkyl, $(C_1-C_6)$alkoxy-$(C_1-C_6)$alkylsulfonyl-$(C_1-C_6)$alkyl, $(C_1-C_6)$alkylcarbonyl-$(C_1-C_6)$alkyl, $(C_1-C_6)$haloalkylcarbonyl-$(C_1-C_6)$alkyl, $(C_1-C_6)$alkoxycarbonyl-$(C_1-C_6)$alkyl, $(C_1-C_6)$haloalkoxycarbonyl-$(C_1-C_6)$alkyl, $(C_1-C_6)$alkylsulfonylamino, aminosulfonyl-$(C_1-C_6)$alkyl, $(C_1-C_6)$alkylaminosulfonyl-$(C_1-C_6)$alkyl, di$(C_1-C_6)$alkylaminosulfonyl-$(C_1-C_6)$alkyl, or is $(C_1-C_6)$alkyl, $(C_1-C_6)$alkoxy, $(C_2-C_6)$alkenyl, $(C_2-C_6)$alkynyl, $(C_3-C_8)$cycloalkyl, each of which is optionally mono- or polysubstituted by identical or different substituents from the group consisting of aryl, hetaryl and heterocyclyl, where aryl, hetaryl or heterocyclyl may each optionally be mono- or polysubstituted by identical or different substituents from the group consisting of halogen, cyano, nitro, hydroxyl, amino, carboxy, carbamoyl, aminosulfonyl, $(C_1-C_6)$alkyl, $(C_3-C_6)$cycloalkyl, $(C_1-C_6)$alkoxy, $(C_1-C_6)$haloalkyl, $(C_1-C_6)$haloalkoxy, $(C_1-C_6)$alkylthio, $(C_1-C_6)$alkylsulfinyl, $(C_1-C_6)$alkylsulfonyl, $(C_1-C_6)$alkylsulfimino, $(C_1-C_6)$alkylsulfimino-$(C_1-C_6)$alkyl, $(C_1-C_6)$alkylsulfimino-$(C_2-C_6)$alkylcarbonyl, $(C_1-C_6)$alkylsulfoximino, $(C_1-C_6)$alkylsulfoximino-$(C_1-C_6)$alkyl, $(C_1-C_6)$alkylsulfoximino-$(C_2-C_6)$alkylcarbonyl, $(C_1-C_6)$alkoxycarbonyl, $(C_1-C_6)$alkylcarbonyl, $(C_3-C_6)$trialkylsilyl and benzyl, $R^3$ is hydrogen, cyano, halogen, nitro, acetyl, hydroxyl, amino, SCN, tri$(C_1-C_6)$alkylsilyl, $(C_3-C_8)$cycloalkyl, $(C_3-C_8)$cycloalkyl-$(C_3-C_8)$cycloalkyl, $(C_1-C_6)$alkyl-$(C_3-C_8)$cycloalkyl, halo$(C_3-C_8)$cycloalkyl, cyano$(C_3-C_8)$cycloalkyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-C_6)$alkylthio, $(C_1-C_6)$alkylthio-$(C_1-C_6)$alkyl, $(C_1-C_6)$alkylsulfinyl, $(C_1-C_6)$haloalkylsulfinyl, $(C_1-C_6)$alkoxy-$(C_1-C_6)$alkylsulfinyl, $(C_1-C_6)$alkylsulfinyl-$(C_1-C_6)$alkyl, $(C_1-C_6)$alkylsulfonyl, $(C_1-C_6)$haloalkylsulfonyl, $(C_1-C_6)$alkoxy-$(C_1-C_6)$alkylsulfonyl, $(C_1-C_6)$alkylsulfonyl-$(C_1-C_6)$alkyl, $(C_1-C_6)$alkylsulfonyloxy, $(C_1-C_6)$alkylcarbonyl, $(C_1-C_6)$alkylthiocarbonyl, $(C_1-C_6)$haloalkylcarbonyl, $(C_1-C_6)$alkylcarbonyloxy, $(C_1-C_6)$alkoxycarbonyl, $(C_1-C_6)$haloalkoxycarbonyl, aminocarbonyl, $(C_1-C_6)$alkylaminocarbonyl, $(C_1-C_6)$alkylaminothiocarbonyl, di$(C_1-C_6)$alkylaminocarbonyl, di$(C_1-C_6)$alkylaminothiocarbonyl, $(C_2-C_6)$alkenylaminocarbonyl, di$(C_2-C_6)$-alkenylaminocarbonyl, $(C_3-C_8)$cycloalkylaminocarbonyl, $(C_1-C_6)$alkylsulfonylamino, $(C_1-C_6)$alkylamino, di$(C_1-C_6)$alkylamino, aminosulfonyl, $(C_1-C_6)$alkylaminosulfonyl, di$(C_1-C_6)$alkylaminosulfonyl, $(C_1-C_6)$alkylsulfoximino, aminothiocarbonyl, $(C_1-C_6)$alkylaminothiocarbonyl, di$(C_1-C_6)$alkylaminothiocarbonyl, $(C_3-C_8)$cycloalkylamino, —NHCO—$(C_1-C_6)$alkyl $((C_1-C_6)$alkylcarbonylamino) or is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, tri$(C_1-C_6)$alkylsilyl, $(C_1-C_6)$alkyl, $(C_1-C_6)$haloalkyl, $(C_1-C_6)$cyanoalkyl, $(C_1-C_6)$hydroxyalkyl, hydroxycarbonyl-$(C_1-C_6)$-alkoxy, $(C_1-C_6)$alkoxycarbonyl-$(C_1-C_6)$alkyl, $(C_1-C_6)$alkoxy-$(C_1-C_6)$alkyl, $(C_2-C_6)$alkenyl, $(C_2-C_6)$haloalkenyl, $(C_2-C_6)$cyanoalkenyl, $(C_2-C_6)$alkynyl, $(C_2-C_6)$haloalkynyl, $(C_2-C_6)$cyanoalkynyl, $(C_1-C_6)$alkoxy, $(C_1-C_6)$haloalkoxy, $(C_1-C_6)$cyanoalkoxy, $(C_1-C_6)$alkoxycarbonyl-$(C_1-C_6)$alkoxy, $(C_1-C_6)$alkoxy-$(C_1-C_6)$alkoxy, $(C_1-C_6)$alkylhydroxyimino, $(C_1-C_6)$alkoxyimino, $(C_1-C_6)$alkyl-$(C_1-C_6)$alkoxyimino, $(C_1-C_6)$haloalkyl-$(C_1-C_6)$alkoxyimino, $(C_1-C_6)$alkylthio, $(C_1-C_6)$haloalkylthio, $(C_1-C_6)$alkoxy-$(C_1-

C$_6$)alkylthio, (C$_1$-C$_6$)alkylthio-(C$_1$-C$_6$)alkyl, (C$_1$-C$_6$)alkylsulfinyl, (C$_1$-C$_6$)haloalkylsulfinyl, (C$_1$-C$_6$)alkoxy-(C$_1$-C$_6$)alkylsulfinyl, (C$_1$-C$_6$)alkylsulfinyl-(C$_1$-C$_6$)-alkyl, (C$_1$-C$_6$)alkylsulfonyl, (C$_1$-C$_6$)haloalkylsulfonyl, (C$_1$-C$_6$)alkoxyl-(C$_1$-C$_6$)alkylsulfonyl, (C$_1$-C$_6$)alkylsulfonyl-(C$_1$-C$_6$)alkyl, (C$_1$-C$_6$)alkylsulfonyloxy, (C$_1$-C$_6$)alkylcarbonyl, (C$_1$-C$_6$)haloalkylcarbonyl, (C$_1$-C$_6$)alkylcarbonyloxy, (C$_1$-C$_6$)alkoxycarbonyl, (C$_1$-C$_6$)haloalkoxycarbonyl, aminocarbonyl, (C$_1$-C$_6$)alkylaminocarbonyl, di(C$_1$-C$_6$)alkylaminocarbonyl, (C$_2$-C$_6$)alkenylaminocarbonyl, di(C$_2$-C$_6$)alkenylaminocarbonyl, (C$_3$-C$_8$)cycloalkylaminocarbonyl, (C$_1$-C$_6$)alkylsulfonylamino, (C$_1$-C$_6$)alkylamino, di(C$_1$-C$_6$)alkylamino, aminosulfonyl, (C$_1$-C$_6$)alkylaminosulfonyl, di(C$_1$-C$_6$)alkylaminosulfonyl, (C$_1$-C$_6$)alkylsulfoximino, aminothiocarbonyl, (C$_1$-C$_6$)alkylaminothiocarbonyl, di-(C$_1$-C$_6$)alkylaminothiocarbonyl or (C$_3$-C$_8$)cycloalkylamino, R$^4$ is hydrogen, cyano, halogen, nitro, acetyl, hydroxyl, amino, SCN, tri(C$_1$-C$_6$)alkylsilyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, halo(C$_3$-C$_8$)cycloalkyl, cyano(C$_3$-C$_8$)cycloalkyl, (C$_1$-C$_6$)alkyl, (C$_1$-C$_6$)haloalkyl, (C$_1$-C$_6$)cyanoalkyl, (C$_1$-C$_6$)hydroxyalkyl, hydroxycarbonyl-(C$_1$-C$_6$)-alkoxy, (C$_1$-C$_6$)alkoxycarbonyl-(C$_1$-C$_6$)alkyl, (C$_1$-C$_6$)alkoxy-(C$_1$-C$_6$)alkyl, (C$_2$-C$_6$)alkenyl, (C$_2$-C$_6$)haloalkenyl, (C$_2$-C$_6$)cyanoalkenyl, (C$_2$-C$_6$)alkynyl, (C$_2$-C$_6$)haloalkynyl, (C$_2$-C$_6$)cyanoalkynyl, (C$_1$-C$_6$)alkoxy, (C$_1$-C$_6$)haloalkoxy, (C$_1$-C$_6$)cyanoalkoxy, (C$_1$-C$_6$)alkoxycarbonyl-(C$_1$-C$_6$)alkoxy, (C$_1$-C$_6$)alkoxy-(C$_1$-C$_6$)alkoxy, (C$_1$-C$_6$)alkylhydroxyimino, (C$_1$-C$_6$)alkoxyimino, (C$_1$-C$_6$)alkyl-(C$_1$-C$_6$)alkoxyimino, (C$_1$-C$_6$)haloalkyl-(C$_1$-C$_6$)alkoxyimino, (C$_1$-C$_6$)alkylthio, (C$_1$-C$_6$)haloalkylthio, (C$_1$-C$_6$)alkoxy-(C$_1$-C$_6$)alkylthio, (C$_1$-C$_6$)alkylthio-(C$_1$-C$_6$)alkyl, (C$_1$-C$_6$)alkylsulfinyl, (C$_1$-C$_6$)haloalkylsulfinyl, (C$_1$-C$_6$)alkoxy-(C$_1$-C$_6$)alkylsulfinyl, (C$_1$-C$_6$)alkylsufinyl-(C$_1$-C$_6$)alkyl, (C$_1$-C$_6$)alkylsulfonyl, (C$_1$-C$_6$)haloalkylsulfonyl, (C$_1$-C$_6$)alkoxy-(C$_1$-C$_6$)alkylsufonyl, (C$_1$-C$_6$)alkylsulfonyl-(C$_1$-C$_6$)alkyl, (C$_1$-C$_6$)alkylsulfonyloxy, (C$_1$-C$_6$)alkylcarbonyl, (C$_1$-C$_6$)alkylthiocarbonyl, (C$_1$-C$_6$)haloalkylcarbonyl, (C$_1$-C$_6$)alkylcarbonyloxy, (C$_1$-C$_6$)alkoxycarbonyl, (C$_1$-C$_6$)haloalkoxycarbonyl, aminocarbonyl, (C$_1$-C$_6$)alkylaminocarbonyl, (C$_1$-C$_6$)alkylaminothiocarbonyl, di(C$_1$-C$_6$)alkylaminocarbonyl, di(C$_1$-C$_6$)alkylaminothiocarbonyl, (C$_2$-C$_6$)alkenylaminocarbonyl, di(C$_2$-C$_6$)alkenylaminocarbonyl, (C$_3$-C$_8$)cycloalkylaminocarbonyl, (C$_1$-C$_6$)alkylsulfonylamino, (C$_1$-C$_6$)alkylamino, di(C$_1$-C$_6$)alkylamino, aminosulfonyl, (C$_1$-C$_6$)alkylaminosulfonyl, di(C$_1$-C$_6$)alkylaminosulfonyl, (C$_1$-C$_6$)alkylsulfoximino, aminothiocarbonyl, (C$_1$-C$_6$)alkylaminothiocarbonyl, di(C$_1$-C$_6$)alkylaminothiocarbonyl, (C$_3$-C$_8$)cycloalkylamino, NHCO—(C$_1$-C$_6$)alkyl, (C$_1$-C$_6$)alkylcarbonylamino), or is aryl or hetaryl, each of which is optionally mono- or polysubstituted by identical or different substituents, where (in the case of hetaryl) at least one carbonyl group may optionally be present and where possible substituents in each case are as follows: cyano, carboxyl, halogen, nitro, acetyl, hydroxyl, amino, SCN, tri(C$_1$-C$_6$)alkylsilyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, halo(C$_3$-C$_8$)cycloalkyl, (C$_1$-C$_6$)alkyl, (C$_1$-C$_6$)haloalkyl, (C$_1$-C$_6$)cyanoalkyl, (C$_1$-C$_6$)hydroxyalkyl, hydroxycarbonyl-(C$_1$-C$_6$)-alkoxy, (C$_1$-C$_6$)alkoxycarbonyl-(C$_1$-C$_6$)alkyl, (C$_1$-C$_6$)alkoxy-(C$_1$-C$_6$)alkyl, (C$_2$-C$_6$)alkenyl, (C$_2$-C$_6$)haloalkenyl, (C$_2$-C$_6$)cyanoalkenyl, (C$_2$-C$_6$)alkynyl, (C$_2$-C$_6$)haloalkynyl, (C$_2$-C$_6$)cyanoalkynyl, (C$_1$-C$_6$)alkoxy, (C$_1$-C$_6$)haloalkoxy, (C$_1$-C$_6$)cyanoalkoxy, (C$_1$-C$_6$)alkoxycarbonyl-(C$_1$-C$_6$)alkoxy, (C$_1$-C$_6$)alkoxy-(C$_1$-C$_6$)alkoxy, (C$_1$-C$_6$)alkylhydroxyimino, (C$_1$-C$_6$)alkoxyimino, (C$_1$-C$_6$)alkyl-(C$_1$-C$_6$)alkoxyimino, (C$_1$-C$_6$)haloalkyl-(C$_1$-C$_6$)alkoxyimino, (C$_1$-C$_6$)alkylthio, (C$_1$-C$_6$)haloalkylthio, (C$_1$-C$_6$)alkoxy-(C$_1$-C$_6$)alkylthio, (C$_1$-C$_6$)alkylthio-(C$_1$-C$_6$)alkyl, (C$_1$-C$_6$)alkylsulfinyl, (C$_1$-C$_6$)haloalkylsulfinyl, (C$_1$-C$_6$)alkoxy-(C$_1$-C$_6$)alkylsulfinyl, (C$_1$-C$_6$)alkylsulfinyl-(C$_1$-C$_6$)alkyl, (C$_1$-C$_6$)alkylsulfonyl, (C$_1$-C$_6$)haloalkylsulfonyl, (C$_1$-C$_6$)alkoxy-(C$_1$-C$_6$)alkylsulfonyl, (C$_1$-C$_6$)alkylsulfonyl-(C$_1$-C$_6$)alkyl, (C$_1$-C$_6$)alkylsulfonyloxy, (C$_1$-C$_6$)alkylcarbonyl, (C$_1$-C$_6$)haloalkylcarbonyl, (C$_1$-C$_6$)alkylcarbonyloxy, (C$_1$-C$_6$)alkoxycarbonyl, (C$_1$-C$_6$)haloalkoxycarbonyl, aminocarbonyl, (C$_1$-C$_6$)alkylaminocarbonyl, di(C$_1$-C$_6$)alkylaminocarbonyl, (C$_2$-C$_6$)alkenylaminocarbonyl, di(C$_2$-C$_6$)alkenylaminocarbonyl, (C$_3$-C$_8$)cycloalkylaminocarbonyl, (C$_1$-C$_6$)alkylsulfonylamino, (C$_1$-C$_6$)alkylamino, di(C$_1$-C$_6$)alkylamino, aminosulfonyl, (C$_1$-C$_6$)alkylaminosulfonyl, di(C$_1$-C$_6$)alkylaminosulfonyl, (C$_1$-C$_6$)alkylsulfoximino, aminothiocarbonyl, (C$_1$-C$_6$)alkylaminothiocarbonyl, di-(C$_1$-C$_6$)alkylaminothiocarbonyl, (C$_3$-C$_8$)cycloalkylamino, (C$_1$-C$_6$)alkylcarbonylamino, R$^5$ is hydrogen, cyano, halogen, nitro, acetyl, hydroxyl, amino, SCN, tri(C$_1$-C$_6$)alkylsilyl, (C$_3$-C$_8$)cycloalkyl, (C$_3$-C$_8$)cycloalkyl-(C$_3$-C$_8$)cycloalkyl, (C$_1$-C$_6$)alkyl-(C$_3$-C$_8$)cycloalkyl, halo(C$_3$-C$_8$)cycloalkyl, (C$_1$-C$_6$)alkyl, (C$_1$-C$_6$)haloalkyl, (C$_1$-C$_6$)cyanoalkyl, (C$_1$-C$_6$)hydroxyalkyl, hydroxycarbonyl-(C$_1$-C$_6$)alkoxy, (C$_1$-C$_6$)alkoxycarbonyl-(C$_1$-C$_6$)alkyl, (C$_1$-C$_6$)alkoxy-(C$_1$-C$_6$)alkyl, (C$_2$-C$_6$)alkenyl, (C$_2$-C$_6$)haloalkenyl, (C$_2$-C$_6$)cyanoalkenyl, (C$_2$-C$_6$)alkynyl, (C$_2$-C$_6$)haloalkynyl, (C$_2$-C$_6$)cyanoalkynyl, (C$_1$-C$_6$)alkoxy, (C$_1$-C$_6$)haloalkoxy, (C$_1$-C$_6$)cyanoalkoxy, (C$_1$-C$_6$)alkoxycarbonyl-(C$_1$-C$_6$)alkoxy, (C$_1$-C$_6$)alkoxy-(C$_1$-C$_6$)alkoxy, (C$_1$-C$_6$)alkylhydroxyimino, (C$_1$-C$_6$)alkoxyimino, (C$_1$-C$_6$)alkyl-(C$_1$-C$_6$)alkoxyimino, (C$_1$-C$_6$)haloalkyl-(C$_1$-C$_6$)alkoxyimino, (C$_1$-C$_6$)alkylthio, (C$_1$-C$_6$)haloalkylthio, (C$_1$-C$_6$)alkoxy-(C$_1$-C$_6$)alkylthio, (C$_1$-C$_6$)alkylthio-(C$_1$-C$_6$)alkyl, (C$_1$-C$_6$)alkylsulfinyl, (C$_1$-C$_6$)haloalkylsulfinyl, (C$_1$-C$_6$)alkoxy-(C$_1$-C$_6$)alkylsulfinyl, (C$_1$-C$_6$)alkylsulfinyl-(C$_1$-C$_6$)alkyl, (C$_1$-C$_6$)alkylsulfonyl, (C$_1$-C$_6$)haloalkylsulfonyl, (C$_1$-C$_6$)alkoxy-(C$_1$-C$_6$)alkylsulfonyl, (C$_1$-C$_6$)alkylsulfonyl-(C$_1$-C$_6$)alkyl, (C$_1$-C$_6$)alkylsulfonyloxy, (C$_1$-C$_6$)alkylcarbonyl, (C$_1$-C$_6$)alkylthiocarbonyl, (C$_1$-C$_6$)haloalkylcarbonyl, (C$_1$-C$_6$)alkylcarbonyloxy, (C$_1$-C$_6$)alkoxycarbonyl, (C$_1$-C$_6$)haloalkoxycarbonyl, aminocarbonyl, (C$_1$-C$_6$)alkylaminocarbonyl, (C$_1$-C$_6$)alkylaminothiocarbonyl, di(C$_1$-C$_6$)alkylaminocarbonyl, di(C$_1$-C$_6$)alkylaminothiocarbonyl, (C$_2$-C$_6$)alkenylaminocarbonyl, di(C$_2$-C$_6$)alkenylaminocarbonyl, (C$_3$-C$_8$)cycloalkylaminocarbonyl, (C$_1$-C$_6$)alkylsulfonylamino, (C$_1$-C$_6$)alkylamino, di(C$_1$-C$_6$)alkylamino, aminosulfonyl, (C$_1$-C$_6$)alkylaminosulfonyl, di(C$_1$-C$_6$)alkylaminosulfonyl, (C$_1$-C$_6$)alkylsulfoximino, aminothiocarbonyl, (C$_1$-C$_6$)alkylaminothiocarbonyl, di(C$_1$-C$_6$)alkylaminothiocarbonyl, (C$_3$-C$_8$)cycloalkylamino or —NHCO—(C$_1$-C$_6$)alkyl ((C$_1$-C$_6$)alkylcarbonylamino) and R$^6$ is (C$_1$-C$_6$)alkyl, (C$_1$-C$_6$)haloalkyl, (C$_1$-C$_6$)cyanoalkyl, (C$_1$-C$_6$)hydroxyalkyl, (C$_1$-C$_6$)alkoxy-(C$_1$-C$_6$)alkyl, $(C_1$-$C_6)$haloalkoxy-$(C_1$-$C_6)$alkyl, $(C_2$-$C_6)$alkenyl, $(C_2$-$C_6)$alkenyloxy-$(C_1$-$C_6)$alkyl, $(C_2$-$C_6)$haloalkenyloxy-$(C_1$-$C_6)$alkyl, $(C_2$-$C_6)$haloalkenyl, $(C_2$-$C_6)$cyanoalkenyl, $(C_2$-$C_6)$alkynyl, $(C_2$-$C_6)$alkynyloxy-$(C_1$-$C_6)$alkyl, $(C_2$-$C_6)$haloalkynyloxy-$(C_1$-$C_6)$alkyl, $(C_2$-$C_6)$haloalkynyl, $(C_2$-$C_6)$cyanoalkynyl, $(C_3$-$C_8)$cycloalkyl, $(C_3$-$C_8)$cycloalkyl-$(C_3$-$C_8)$cycloalkyl, $(C_1$-$C_6)$alkyl-$(C_3$-$C_8)$cycloalkyl, halo$(C_3$-$C_8)$cycloalkyl, $(C_1$-$C_6)$alkylthio-$(C_1$-$C_6)$alkyl, $(C_1$-$C_6)$haloalkylthio-$(C_1$-$C_6)$alkyl, $(C_1$-$C_6)$alkylsulfinyl-$(C_1$-$C_6)$alkyl, $(C_1$-$C_6)$haloalkylsulfinyl-$(C_1$-$C_6)$alkyl, $(C_1$-$C_6)$alkylsulfonyl-$(C_1$-$C_6)$alkyl, $(C_1$-$C_6)$haloalkylsulfonyl-$(C_1$-$C_6)$alkyl, $(C_1$-$C_6)$alkoxy-$(C_1$-$C_6)$alkylthio-$(C_1$-$C_6)$alkyl, $(C_1$-$C_6)$alkoxy-$(C_1$-$C_6)$alkylsulfinyl-$(C_1$-$C_6)$alkyl, $(C_1$-$C_6)$alkoxy-$(C_1$-$C_6)$alkylsulfonyl-$(C_1$-$C_6)$alkyl, $(C_1$-$C_6)$alkylcarbonyl-$(C_1$-$C_6)$alkyl, $(C_1$-$C_6)$haloalkylcarbonyl-$(C_1$-$C_6)$alkyl, $(C_1$-$C_6)$alkoxycarbonyl-$(C_1$-$C_6)$alkyl, $(C_1$-$C_6)$haloalkoxycarbonyl-$(C_1$-$C_6)$alkyl, aminocarbonyl-$(C_1$-$C_6)$alkyl, $(C_1$-$C_6)$alkylamino-$(C_1$-$C_6)$alkyl, di$(C_1$-$C_6)$alkylamino-$(C_1$-$C_6)$alkyl or $(C_3$-$C_8)$cycloalkylamino-$(C_1$-$C_6)$alkyl.

\* \* \* \* \*